(12) United States Patent
Topalian et al.

(10) Patent No.: US 6,951,917 B1
(45) Date of Patent: Oct. 4, 2005

(54) MHC-CLASS II RESTRICTED MELANOMA ANTIGENS AND THEIR USE IN THERAPEUTIC METHODS

(75) Inventors: Suzane L. Topalian, Brookville, MD (US); Steven A. Rosenberg, Potomac, MD (US); Paul F. Robbins, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/533,895

(22) Filed: Sep. 26, 1995

(51) Int. Cl.$^7$ .................. C07K 7/00; C07K 14/705; A01N 63/00; A61K 39/00; A61K 39/385

(52) U.S. Cl. .................. 530/328; 530/324; 530/325; 530/326; 530/327; 530/350; 530/402; 530/403; 424/185.1; 424/192.1; 424/193.1; 424/277.1; 424/93.71

(58) Field of Search .................. 530/324, 325, 530/326, 327, 350, 402, 403, 328, 329, 330; 424/185.1, 192.1, 193.1, 277.1, 93.71

(56) References Cited

U.S. PATENT DOCUMENTS

| 5,262,177 A | 11/1993 | Brown et al. |
| 5,342,774 A | 8/1994 | Boon et al. |
| 5,679,511 A | * 10/1997 | Kwon |
| 5,858,776 A | * 1/1999 | Ostrand-Rosenberg et al. |

FOREIGN PATENT DOCUMENTS

| DE | 3341367 | 5/1984 |
| EP | 0668350 | 8/1995 |
| EP | 0 679 660 A | 11/1995 |
| GB | 2133543 | 8/1984 |
| WO | WO 88/02372 | 4/1988 |
| WO | 9314189 | 7/1993 |
| WO | 9405304 | 3/1994 |
| WO | 9414459 | 7/1994 |
| WO | 9423067 | 10/1994 |
| WO | WO 95 00849 A | 1/1995 |
| WO | 9522561 | 8/1995 |
| WO | WO 95 23234 A | 8/1995 |

OTHER PUBLICATIONS

Rammensee et al (Immunogenetics (1995) 41:175–177).*
Razzaque et al. Vaccine 19:644–647 (2001).*
Rosenberg, Immunology Today 18(4):175–182.*
Janeway et al. Immunbiology (1999) Garland Press NY p. 122.*
Bohinski, Modern Concepts in Biochem., 5th ed., p. 66–68, 1987.*
Salgaller et al. Cancer Immunol. Immunother. 39:105–116, 1994.*
Parker et al. J. Immunol. 149:3580–87, Dec. 1992.*

Englehard, V.H. Current Opinion in Immunology 6:13–23, 1994.*
Burgess et al. J. Cell Biol. 111:2129–38, Nov. 1990.*
Lazar et al. Mol. Cell Biol. 8(3):1247–52, Mar. 1988.*
Chicz, R.M., et al., "Specificity And Promiscuity Among Naturally Processed Peptides Bound To HLA–Dr Alleles"*J. Exp. Med.*, 178, 27–47; (1993).
Sette, A. et al., "Capacity Of Intact Proteins To Bind To MHC Class II Molecules" *J. Immunol.*, 143, 1265–1267; (1989).
Brown, J.H., et al. "Three–Dimensional Structure Of The Human Class II Histocompatability Antigen HLA–DRI"*Nature*, 364, 33–39 (1993).
Kwon, et al., "Isolation And Sequence Of A cDNA Clone For Human Tyrosinanse That Maps At The Mouse c–Albino Locus" *PNAS*, 84:7473–7477, (1987).
Shibihara, S. et al., "Molecular Basis For The Heterogeneity Of Human Tyrosinase" *J. Exp. Med*, 156:403–414, (1988).
Sette, A. et al., "HLA–DR4w4–Binding Motifs Illustrate The Bio chemical Basis Of Degeneracy And Specificity In Peptide–Dr Interactions" *J. Immunol.*, 151:3163–3170, (1993).
Rammensee, H.G. et al., "MHC Ligands And Peptide Motifs: First Listing" *Immunogenetics*, 41:178–228 (1995).
Kozono, H. et al., "Production Of Soluble MHC II Class II Proteins With Covalently Bound Single Peptides" *Nature*, 369:151–154 (1994).
Sinigaglia, F. et al., "Motifs And Super motifs for MHC Class II Binding Peptides" *J. Exp. Med.*, 181:449–451 (1995).
Kawakami, et al., "Cloning Of The Gene Coding For A Shared Human Melanoma Antigen Recognized By Autologous T–Cells Infiltrating Into Tumor" *Proc. Natl. Acad. Sci.*, 91:3575–3579 (1994).
Wang, R–F et al., "Identification Of A Gene Encoding A Melanoma Tumor Antigen Recognized By HLA–A31–Resricted Tumor Infiltrating Lumpitocytes" *J. Exp. Med.*, 181:799–804, (1995).
Sidney, J. et al., "DR B1* 0301 Molecules Recognize A Structural Motif Distinct From The One Recognized By Most DR B, Alleles" *J. Immunol.*, 149, 2634–2640, (1992).

(Continued)

*Primary Examiner*—Christina Chan
*Assistant Examiner*—F. Pierre Vandervegt
(74) *Attorney, Agent, or Firm*—Leydig, Voit & Mayer, Ltd.

(57) ABSTRACT

The present invention provides MHC Class II restricted melanoma antigens recognized by CD4$^+$ T cells. This invention further provides prophylactic and therapeutic applications for the Class II restricted melanoma antigens. In particular, this invention provides tyrosinase Class II restricted melanoma antigens, as well as tyrosinase immunogenic peptides which have been modified to enhance their immunogenicity. These antigens can serve as an immunogens or vaccines to prevent or treat melanoma. In addition a method for isolating Class II restricted melanoma antigens or identifying new Class II restricted melanoma antigens is provided.

61 Claims, 12 Drawing Sheets

OTHER PUBLICATIONS

Malcherek, G. et al., "Super Motifs Enable Natural Invariant Chain–derived Peptides To Interact With Many Major Histocompatability Complex–class II Molecules" *J. Exp. Med.*, 181, 527–536 (1995).

Topalian, S., "MHC Class II Restricted Tumor Antigens And The Role Of CD4+ T Cells In Cancer Antigens" *Current Opinion in Immunology*, 6:741–745, (1994).

Topalian, S., et al. (1994) "Melanoma Specific CD4+ T–Lymphocytes Recognize Human Melanoma Antigens Processed And Presented By Epstein Barr Virus Transformed Cells" *Int. J. Cancer* 58:69–79.

Nanda, et al., "Induction of Anti Self–Immunity to Bone Cancer" *Cell*, 82:13–17, (1995).

Markus, N. et al., "*Analysis of Cytokine Secretion by Melanoma–Specific CDY & Lymphocytes*" *Journal of Interferon and Cytokine Research*, 15:739–746, (1995).

GenBank, Acession No. J03581—Jan. 14, 1995.

GenBank, Acession No. U01873—Sep. 27, 1993.

GenBank, Acession No. Y00819—Jul. 28, 1995.

GenBank, Acession No. M27160—Jul. 28, 1995.

Coulie, P.G. et al. (1993) "Genes coding for tumor antigens recognized by cytolytic T–lymphocytes." *J. Immunotherap.*; 14:104–109.

Coulie P.G. et al. "A new gene coding for a differentiation antigen recognized by autologous cytolytic T lymphocytes on HLA–A2 melanomas." *J. Exp. Med.* 1994; 180:35–42.

Maresh, C.A. et al.: "Cloning and expression of the gene for the melanoma associated ME20 antigen." *DNA and Cell Biology* 1994; 13:87–95.

Cox, A.L., et al. "Identification of a peptide recognized by five melanoma–specific human cytotoxic T cell lines." *Science* 1994; 264:716–719.

Brichard, V., et al.: "The tyrosinase gene codes for an antigen recognized by autologous cytolytic T lymphocytes on HLA–A2 melanomas". *J. Exp. Med.* 1993; 178:489–495.

Gaugler, B., et al. "Human gene MAGE–3 codes for an antigen recognized on a mnelanoma by autologous cytolytic T lymphocytes". *J. Exp. Med.* 1994; 179:921–930.

Traversari, C., et al.: "A nonpeptide encoded by human gene MAGE–1 is recognized on HLA–A1 by cytolytic T lymphocytes directed against tumor antigen MZ2–E". *J. Exp. Med.* 1992; 176:1453–1457.

Cellis, E., et al.: "Induction of anti–tumor cytotoxic T lymphocytes in normal humans using primary cultures and synthetic peptides epitopes". *Proc. Natl. Acad. Sci. USA* 1994; 91:2105–2109.

Boon, T.: "Toward a genetic analysis of tumor rejection antigens". *Adv. Cancer Res.* 1992; 58:177–210.

Kawakami, Y., et al.: "T–cell recognition of human melanoma antigens." *J. Immunother.* 1993; 14:88–93.

Bakker, A.B.H., et al.: "Melanocyte lineage–specific antigen gp100 is recognized by melanocyte–derived tumor infiltrating lymphocytes." *J. Exp. Med.* 1994; 179:1005–1009.

Wölfel, T., et al.: "Two tyrosinase nonapeptides recognized on HLA–A2 melanomas by autologous cytolytic T. lymphocytes." *Eur. J. Immunol.* 1994; 24:759–764.

Rosenberg, S.A., et al.: "Use of tumor infiltrating lymphocytes and interleukin–2 in the immunotherapy of patients with metastatic melanoma. Preliminary report." *N. Engl. J. Med.* 1988; 319:1676–1680.

Kawakami, Y., et al.,: "Shared human melanoma antigens. Recognition by tumor infiltrating lymphocytes in HLA–A2.1 transfected melanomas." *J. Immunol* 1992; 148:638–643.

Van der Bruggen, et al.: "A gene encoding an antigen recognized by cytolytic T. lymphocytes on a human melanoma." *Science* 1991; 254:1643–1647.

Falk, K., et al.: "Allele–specific motifs revealed by sequencing of self–peptides eluted from MHC molecules." *Nature* 1991; 351:290–296.

Kubo, R., et al.: "Definition of specific peptide motifs for four major HLA–A Alleles." *Journal of Immunology* 1994, 152:3913–3924.

Parker, K., et al.: "Sequence motifs important for peptide binding to the human MHC class 1 molecule. HLA–A2." *J. Immunol.* 1992; 3580–3587.

Ruppert, J., et al.: "Prominent role of secondary anchor residues in peptide binding to HLA–A2.1 molecules." *Cell* 1993; 74:929–937.

Storkus, W., et al.: "Identification of human melanoma peptides recognized by class 1 restricted tumor infiltrating T lymphocytes." *Journal of Immunology* 1993; 151:3719–3727.

Kawakami, Y., et al.: "Cloning of the gene coding for a shared human melanoma antigen recognized by autologous T cells infiltrating into tumor." *Pro. Natl. Acad. Sci. USA* 1994; 91:3515–3519.

Adema, G.J. et al., "Molecular characterization of the melanocyte lineage–specific antigen gp100." *Journal of Biological Chemistry* 1994; 269:20126–20133.

EMBL Database Acession No. M32295: 26–11–90 Vogel A.: Human KD melanocyte specific secreted glycoprotein MRNA 3'end'.

Kawakami, Y., et al.: "Identification of a human melanoma antigen recognized by tumor–infiltrating lymphocytes associated with in vivo tumor rejection." *Proc. Natl. Acad. Sci. USA* 1994; 91:6458–6462.

Kawakami, Y., et al., "Identification of the Immunodominant Peptides of the MART–1 Human Melanoma Antigen Recognized by the Majority of HLA–A2–restricted Tumor Infiltrating Lymphocytes" *J. Exp. Med.* 180:347–352, 1994.

Rivoltini, L., et al., "Induction of Tumor–Reactive CTL from Peripheral Blood and Tumor–Infiltrating Lymphocytes of Melanoma Patients by In Vitro Stimulation with an Immunodominant Peptide of the Human Melanoma Antigen MART–1" *Journal of Immunology*, 1995, 154:2257–2265.

Slingluff, C.L.,Jr., et al., "Direct analysis of tumor–associated peptide antigens" *Current Opinion in Immunology* 1994, 6:733–740.

Cole, D.J. et al., "Characterization of the Functional Specificity of a Cloned T–Cell Receptor Heterodimer Recognizing the MART–1 Melanoma Antigen" *Cancer Res.* 55:748–752 Feb. 1995.

Cole, D.J., et al., "Identification of MART–1–specific T–Cell Receptors: T Cells Utilizing Distinct T–Cell Receptor Variable and Joining Regions Recognize the Same Tumor Epitope" *Cancer Res.* 54:5265–5268, 1994.

Castelli, C., et al., "Mass Spectrometric Identification of a Naturally Processed Melanoma Peptide Recognized by $CD8^+$ Cytotoxic T Lymphocytes" *J. Exp. Med.* 181:363–368 1995.

Sette, A., et al., "Peptide Binding To The Most Frequent HLA–A Class I Alleles Measured By Quantitative Molecular Binding Assays" *Molecular Immunology* 31:813–822, 1994.

Wölfel, T., et al., "Analysis Of Antigens Recognized On Human Melanoma Cells By A2–Restricted Cytolytic T Lymphocytes (CTL)" *Int. J. Cancer* 55:237–244, 1993.

Wölfel, T., et al., "Isolation Of Naturally Processed Peptides Recognized By Cytolytic Lymphocytes (CTL) On Human Melanoma Cells In Association With HLA–A2.1" *Int. J. Cancer* 57:413–418, 1994.

Topalian, S.L., et al., "Human CD4 +T Cells Specifically Recognize a Shared Melanoma–Associated Antigen Encoded by the Tyrosinase Gene" *PNAS* 91:9461–9465, 1994.

Boël, P., et al., "BAGE: a New Gene Encoding an Antigen Recognized on Human Melanomas by Cytolytic T Lymphocytes" *Immunology* 2:167–175 1995.

Slingluff, C.L., Jr., et al., "Recognition of Human Melanoma Cells by HLA–A2.1–Restricted Cytotoxic T Lymphocytes Is Mediated by a Least Six Shared Peptide Epitopes" *Journal of Immunology* 150:2955–2963 1993.

Genbank Database Accession No. M77348—Human PMEL 17 in RNA—Nov. 14, 1991.

Genbank Database Accession No. U06654—Human Differentiation Antigen Melan–A Protein in RNA Jul. —30, 1994.

Genbank Database Accession No. U06452—Human Melanoma Antigen Recognized by T–Cells (MART–1) MRNA—Jun. 25, 1994.

Genbank Database Accession No. S73003—GP100 Melanocyte Lineage Specific Antigen / PMELL 7—Jan. 25, 1995.

Genbank Database Accession No. U01874—Human ME20 MRNA May 27, 1994.

Bouchard, Brigitte, et al.: "Induction of pigmentation in mouse fibroblasts by expression of human tryosinance." *J. Exp. Med.* 1989; 169:2029–2042.

Tripathi, Ram K., et al.: "Tyrosinase Gene Mutations in Type I (Tyrosinase–Deficient) Oculocutaneous Albinism Define Two Clusts of Missense Substitutions." *American Journal of Medical Genetics* 1992; 43:865–871.

Oetting, William S. and King, Richard A.: "Molecular Basis of Type I (Tyrosinase–Related) Oculocutaneous Albinism: Mutations and Polymorphisms of the Human Tyrosinase Gene." *Human Mutation* 1993; 2:1–6.

Spritz, Richard A.: "Molecular Genetics of Oculocutaneous Albinism." *Seminars in Dermatology* 1993; vol. 12, No. 3:167–172.

Robbins, et al. (1994), "Recognition of tyrosinase by tumor-infiltating lymphocates from a patient responding to immunotherapy", *Cancer Research*; 54:3124–3126.

Robbins, et al (1995), "Cloning of a new gene encoding an antigen recognized by melanoma–specific HLA–A24–restricted tumor–infiltrating lymphocytes" *J. Immunol.*1995;154(11), 5944, 50.

Adema, G.J., et al.: "Melanocyte lineage–specific antigens recognized by monoclonal antibodies NK1–beteb, HMB–50, and HMB–45 are encoded by a single cDNA." *Am J. Pathol.* 1993; 143:1579–1585.

Kwon, B.S., et al.: "A melanocyte–specific gene, Pmel 17, maps near the silver coat color locus on mouse chromosome 10 and is in a syntenic region on human chromosome 12." *Proc. Natl. Acad. Sci. USA* 1991; 88:9228–9232.

Rivoltini, L., et al., "Induction of Tumor–Reactive CTL from Periphcral Blood and Tumor–Infiltrating Lymphocytes of Melanoma Patients by In Vitro Stimulation with an Immunotominant Peptide of the Human Melanoma Antigen MART–1" *Journal of Immunology*, 1995, 154:2257–2265.

Slingluff, C.L., Jr., et al., "Direct analysis of tumor–associated peptide antigens" *Current Opinion in Immunology* 1994, 6:733–740.

Cole, D.J., et al., "Characterization of the Functional Specificity of a Cloned T–Cell Receptor Heterodimer Recognizing the MART–1 Melanoma Antigen" *Cancer Res.* 55:748–752 Feb. 1995.

Genbank Database Accession No. M77348—Human PMEL 17 in RNA—Jan. 8, 1995.

Topalian, et al., "Melanoma–specific CD4+ T Cells Recognize Nonmutated HLA–DR–restricted Tyrosinase Epitopes", *Journal of Experimental Medicine*, 183:1965–1971 (1996).

* cited by examiner

HLA Restriction of Tyrosinase Recognition
by CD4⁻ TIL 1088
(GM-CSF secretion, pg/ml/24 hr)

| Antigen Presenting Cells | Antigen Presented | | | | HLA-DRβ1* | |
|---|---|---|---|---|---|---|
| | None | 1088-mel lysate | Ty 56-70 (A63→V) | Ty 448-462 (D456→V) | | |
| Experiment 1 | | | | | | |
| 1088-EBV | 145 | 1179 | 2445 | 2969 | 0301 | 0401 |
| 697-EBV | 282 | 1014 | >500 | 3815 | 0401 | 1501 |
| BM14 | 751 | 3282 | 4793 | 5121 | 0401 | - |
| 860-EBV | 376 | 870 | 383 | 345 | 0301 | 1301 |
| 583-EBV | 484 | 550 | 574 | 477 | 0404 | 1501 |
| 1087-EBV | 507 | 557 | 550 | 566 | 0701 | 1201 |
| Experiment 2 | | | | | | |
| 1359-EBV | 183 | 2238 | 1179 | 1714 | 0301 | 0401 |
| BM14 | 372 | 2822 | 1892 | 2805 | 0401 | - |
| 1485-EBV | 171 | 160 | 154 | 222 | 0407 | 1501 |
| COX | 544 | 482 | 735 | 703 | 0301 | - |
| PGF | 54 | 150 | 76 | 46 | 1501 | - |

Antigen presenting cells pulsed with tumor lysate or 100 uM peptide overnight,
then washed prior to assay, all cells at 1x10⁶/ml

FIGURE 5

Determining the P1 and P6 Anchor Positions for Ty 56-70

|  |  | GM-CSF (pg/ml/24h.) | | |
|---|---|---|---|---|
|  |  | Exp. 1 | Exp. 2 | Exp. 3 |
| Ty 56-70 | Q N I L L S N A P L G P Q F P | 295 | 524 | 903 |
|  | Seq Id No: 1 | | | |
| I58 | - - Q - - - - - - - - - - - - | <8 | <8 | <8 |
|  | - - F - - - - - - - - - - - - | 39 | 46 | ND |
|  | - - V - - - - - - - - - - - - | ND | ND | 154 |
| L59 | - - - Q - - - - - - - - - - - | <8 | <8 | <8 |
|  | - - - F - - - - - - - - - - - | <8 | <8 | ND |
|  | - - - V - - - - - - - - - - - | ND | ND | <8 |
| L60 | - - - - Q - - - - - - - - - - | <8 | 62 | <8 |
|  | - - - - F - - - - - - - - - - | 86 | <8 | ND |
|  | - - - - V - - - - - - - - - - | ND | ND | 10 |
| A63 | - - - - - - - Q - - - - - - - | <8 | <8 | ND |
|  | - - - - - - - V - - - - - - - | 889 | 2080 | ND |
| P64 | - - - - - - - - Q - - - - - - | <8 | <8 | ND |
|  | - - - - - - - - V - - - - - - | <8 | 48 | ND |
| L65 | - - - - - - - - - Q - - - - - | 24 | 50 | ND |
|  | - - - - - - - - - V - - - - - | 2050 | 3816 | ND |
| Ty 57-70 | - - - - - - - - - - - - - - - | ND | ND | 615 |
| Ty 58-70 | - - - - - - - - - - - - - - - | ND | <8 | <8 |
| Ty 59-71 | - - - - - - - - - - - - - - → | ND | <8 | <8 |
| Ty 60-72 | - - - - - - - - - - - - - - → | ND | <8 | <8 |
| Ty 61-75 | - - - - - - - - - - - → | ND | <8 | ND |
| 1088 mel Lysate |  | 6762 | >5500 | ND |

TIL & EBV backgrounds for Exp.1=53, Exp.2=296, Exp.3=99 pg/ml.
These have been subtracted from the numbers shown above.

Q N [I] L L S N [A] P L G P Q F P   SEQ ID No: 1

Ty 448-462

D Y S [Y] L Q D S [D] P D S F Q D   SEQ ID No: 6

FIGURE 7

Determining the P1 Anchor for Ty 448-462

|  |  | GM-CSF (pg/ml/24h.) | |
|---|---|---|---|
|  |  | Exp. 1 | Exp. 2 |
| Ty 448-462 | D Y S Y L Q D S D P D S F Q D | 108 | 802 |
|  | SEQ ID No: 6 | | |
| Y449 | - Q - - - - - - - - - - - - - | 74 | 520 |
|  | - F - - - - - - - - - - - - - | 103 | 781 |
| Y451 | - - - Q - - - - - - - - - - - | 28 | <8 |
|  | - - - F - - - - - - - - - - - | 324 | 1065 |
| L452 | - - - - Q - - - - - - - - - - | 14 | <8 |
|  | - - - - F - - - - - - - - - - | 14 | <8 |
| Ty 449-462 | - - - - - - - - - - - - - - - | 485 | 1960 |
| Ty 450-462 | - - - - - - - - - - - - - - | 556 | 2749 |
| Ty 451-462 | - - - - - - - - - - - - - | 21 | <8 |
| Ty 452-462 | - - - - - - - - - - - - | 18 | <8 |
| 1088-nel Lysate |  | >5500 | 5822 |

TIL & EEV backgrounds for Exp.1=52 and Exp.2=196 pg/ml.
These have been subtracted from the numbers shown above.

FIGURE 9

MHC-CLASS II RESTRICTED MELANOMA ANTIGENS AND THEIR USE IN THERAPEUTIC METHODS

FIELD OF THE INVENTION

This invention is in the field of prevention and treatment of human cancers. More specifically, this invention relates to MHC Class II restricted melanoma antigens recognized by helper T Cells and to the preventative, and therapeutic applications which employ these antigens. This invention also relates to methods for determining Class II restricted melanoma antigens.

BACKGROUND OF THE INVENTION

Melanomas are aggressive, frequently metastatic tumors derived from either melanocytes or melanocyte related nevus cells ("Cellular and Molecular Immunology" (1991) (eds) Abbas A. K., Lechtman, A. H., Pober, J. S.; W. B. Saunders Company, Philadelphia: pages 340–341). Melanomas make up approximately three percent of all skin cancers and the worldwide increase in melanoma is unsurpassed by any other neoplasm with the exception of lung cancer in women ("Cellular and Molecular Immunology" (1991) (eds) Abbas, A. K., Lechtiman, A. H., Pober, J. S.; W. B. Saunders Company Philadelphia pages: 340–342; Kirkwood and Agarwala (1993) *Principles and Practice of Oncology* 7:1–16). Even when melanoma is apparently localized to the skin, up to 30%; of the patients will develop systemic metastasis and the majority of these will die (Kirkwood and Agarwala (1993) *Principles and Practice of Oncology* 7:1–16). Classic modalities of treating melanoma include surgery, radiation and chemotherapy. In the past decade immunotherapy and gene therapy have emerged as new and promising methods for treating melanoma (*Biologic Therapy of Cancer*, 2nd ed. (1995) Devita, V. T., Hellman, S, and Rosenberg, S. A., eds; J. B. Lippincott Co., Philadelphia).

Shared melanoma-associated antigens (Ag) expressed among a variety of melanoma patients can be recognized by cytotoxic $CD8^+$ T lymphocytes derived from melanoma patients. In short-term lysis assays, cytotoxic T lymphocytes (CTL) grown from in vitro sensitized peripheral blood lymphocytes (PBL) or lymph node lymphocytes, or from lymphocytes infiltrating metastatic melanoma lesions, have been shown to recognize autologous and MHC class I compatible allogeneic melanomas but not HLA-matched nonmelanoma tumors, lymphoblasts, or cultured fibroblasts (Darrow, D. L., Slingluff, C. L., & Siegler, H. F. (1989.) *J. Immunol.* 142, 3329–3335; Hom, S. S., et al. (1991) *J. Immunother.* 10, 153–164). Similar recognition patterns have been observed by measuring cytokine secretion from tumor infiltrating lymphocytes (TIL) cocultivated with autologous or HLA-matched allogeneic tumor stimulators (Hom, S. S., et al. (1993) *J. Immunother.* 13, 18–30). Recently, melanoma-specific HLA-A2 restricted CTL clones have been shown to recognize cultured normal melanocytes as well as their malignant counterparts, suggesting that shared melanoma antigens can be lineage specific (Anichini, A., et al. (1993) *J. Exp. Med.* 177, 989–998). To date, several class I-restricted melanoma-associated antigens have been molecularly defined (Van Der Bruggen, P., et al. (1991) *Science* 254, 1643–1647; Brichard, V., et al. (1993) *J. Exp. Med.* 178, 489–495; Kawakami, Y., et al. (1994) *Proc. Natl. Acad. Sci. USA*. 91, 3515–3519; Bakker, A. B. H., et al. (1994) *J. Exp. Med.* 179, 1005–1009; Kawakami, Y., et al. (1994) *Proc. Natl. Acad. Sci. USA*. 91,6458–6462; Gaugler B., et al. (1994) *J. Exp. Med.* 179, 921–930). These antigens and derivative class I-restricted peptides 8 to 10 amino acids in length are currently being developed as clinical vaccines to stimulate $CD8^+$ T cell responses against melanoma.

While animal models of malignant and viral diseases have shown the importance of $CD8^+$ T cells in the effector phase of the immune response, the $CD4^+$ helper arm has been shown to mediate critical priming and effector functions as well. T cell receptors on $CD4^+$ T cells recognize a complex consisting of an antigenic peptide in conjunction with an MHC Class II molecule. Unlike peptides binding to MHC class I molecules, which are restricted in length from 8–10 amino acids, the antigenic peptides that bind Class II range from about 10 to about 34 amino acids in length and even entire proteins. (Chicz, R. M. et al (1993) *J. Exp. Med.* 178, 27–47; Sette, A. et al (1989) *J. Immunol* 143, 1265–1267.) This is due to the structure of the peptide binding groove in MHC class II molecules, which is open at both ends and allows for overhang of longer peptides outside of the critical binding core. In contrast, the peptide binding groove in MHC class I molecules is closed at both ends, strictly limiting the length of possible binding peptides. (Brown, J. H. et al (1993) *Nature* 364, 33–39).

Strong and long lasting immunity depends in part on $CD4^+$ helper T cell functions. Therefore the identification of Class II-restricted melanoma antigens will broaden the immunotherapeutic approaches to treating and/or prophylaxing against melanoma.

SUMMARY OF THE INVENTION

This invention relates, in general, to MHC Class II restricted melanoma antigens recognized by $CD4^+$ T-lymphocytes and the nucleic acid sequences encoding these antigens. This invention also provides therapeutic uses for the nucleic acid sequences, proteins or peptides described herein. In addition, this invention provides a method for identifying additional Class II restricted melanoma antigens.

It is a general object of the present invention to provide proteins, polypeptides or peptides which encode for Class II restricted melanoma antigens.

It is another object of this invention to provide a recombinant molecule comprising a vector and all or part of the nucleic acid sequence encoding for a Class II restricted melanoma antigen.

It is another object of this invention to produce recombinant proteins or peptides encoded by all or part of the nucleic acid sequence encoding for a Class II restricted melanoma antigen.

It is a further object of this invention to provide methods for prophylactic or therapeutic uses for the Class II restricted melanoma antigens.

It is also an object of this invention to provide melanoma vaccines comprising all or part of the Class II restricted melanoma antigens.

It is a further object of this invention to provide immunogenic peptides demonstrated to be Class II restricted melanoma antigens for use in vaccines.

It is a particular object of this invention to provide tyrosinase peptides which are Class II restricted melanoma antigens.

In addition, it is another object of this invention to provide multivalent vaccines comprising at least one Class II restricted melanoma antigen and at least one other immunogenic molecule capable of eliciting an immune response in a mammal to melanoma antigens.

It is another object of this invention to provide a method for preventing or treating melanoma utilizing Class II restricted melanoma antigens in gene therapy protocols.

It is a further object of this invention to provide peptides derived from a tyrosinase protein sequence for use in vaccines.

It is yet another object of this invention to provide a method of prophylactic or therapeutic immunization for melanoma using the vaccines described herein.

It is a further object of this invention to provide a method of identifying Class II restricted melanoma antigens that would constitute potential targets for immunotherapy.

DESCRIPTION OF THE FIGURES

FIG. 5 shows the MHC Class II restriction of tyrosinase peptide recognition by CD4+ TIL 1088 cells. The antigen presenting cells were pulsed with autologous melanoma lysate or 100 μM peptide overnight then washed prior to assay, all cells at 1×10$^6$/ml. HLA-DR-B1*0401 was identified as the presenting MHC molecule for Ty 56-70 and Ty 448-462.

FIG. 6 shows in three separate experiments, CD4+ T cells from patient 1088 showed specific recognition of the Ty 56-70 peptide. Mutated and truncated peptides were used to identify the primary anchor (binding) residues within Ty 56-70. Recognition was measured as GM-CSF secretion by T cells cocultured for 24 hours with peptide-pulsed autologous EBV-transformed B cells. Sequence identifiers for FIG. 6: Ty 56-70, SEQ ID NO: 1; Ty 56-70 I58→Q, SEQ ID NO: 17; Ty 56-70 I58→F, SEQ ID NO: 18; Ty 56-70 I58→V, SEQ ID NO: 19; Ty 56-70 L59→Q, SEQ ID NO: 20; Ty 56-60 L59→F, SEQ ID NO: 21; Ty 56-70 L59→V, SEQ ID NO: 22 Ty 56-70 L60→Q, SEQ ID NO: 23 Ty 56-70 L60→F, SEQ ID NO: 24; Ty 56-70 L60→V, SEQ ID NO: 25; Ty 56-70 A63→Q, SEQ ID NO: 26; Ty 56-70 A63→V, SEQ ID NO: 5; Ty 56-70 P64→Q, SEQ ID NO: 27; Ty 56-70 P64→V, SEQ ID NO: 28; Ty 56-70 L65→Q, SEQ ID NO: 29; Ty 56-70 L65→V, SEQ ID NO: 3; Ty 57-70, SEQ ID NO: 2; Ty 58-70, SEQ ID NO: 30; Ty 59-71, SEQ ID NO: 31; Ty 60-72, SEQ ID NO: 32; Ty 61-75, SEQ ID NO: 33.

FIG. 7 shows the tyrosinase (Ty) peptides Ty 56-70 and Ty 448-462 with the P1 and P6 anchor positions boxed. The number designation of the peptide (e.g. Ty 56-70) indicates the amino acids spanned by the peptide, with 1 being the methionine encoded by the initiation codon.

FIG. 9 shows in two experiments, Ty 448-462 was specifically recognized by CD4+ T cells from patient 1088. Mutated and truncated peptides were used to identify Y451 as the primary P1 binding residue within Ty 448-462. Sequence identifiers for FIG. 9: Ty 448-462, SEQ ID NO: 6; Ty 448-462 Y449→Q, SEQ ID NO: 8; Ty 448-462 Y449→F, SEQ ID NO: 9; Ty 448-462 Y451→Q, SEQ ID NO: 34; Ty 448-462 Y451→F, SEQ ID NO: 10; Ty 448-462 L452→Q, SEQ ID NO: 35; Ty 448-462 L452→F, SEQ ID NO: 36; Ty 449-462, SEQ ID NO: 13; Ty 450-462, SEQ ID NO: 14; Ty 451-462, SEQ ID NO: 37; Ty 452-462, SEQ ID NO: 38.

DETAILED DESCRIPTION OF THE INVENTION

Figure 1:
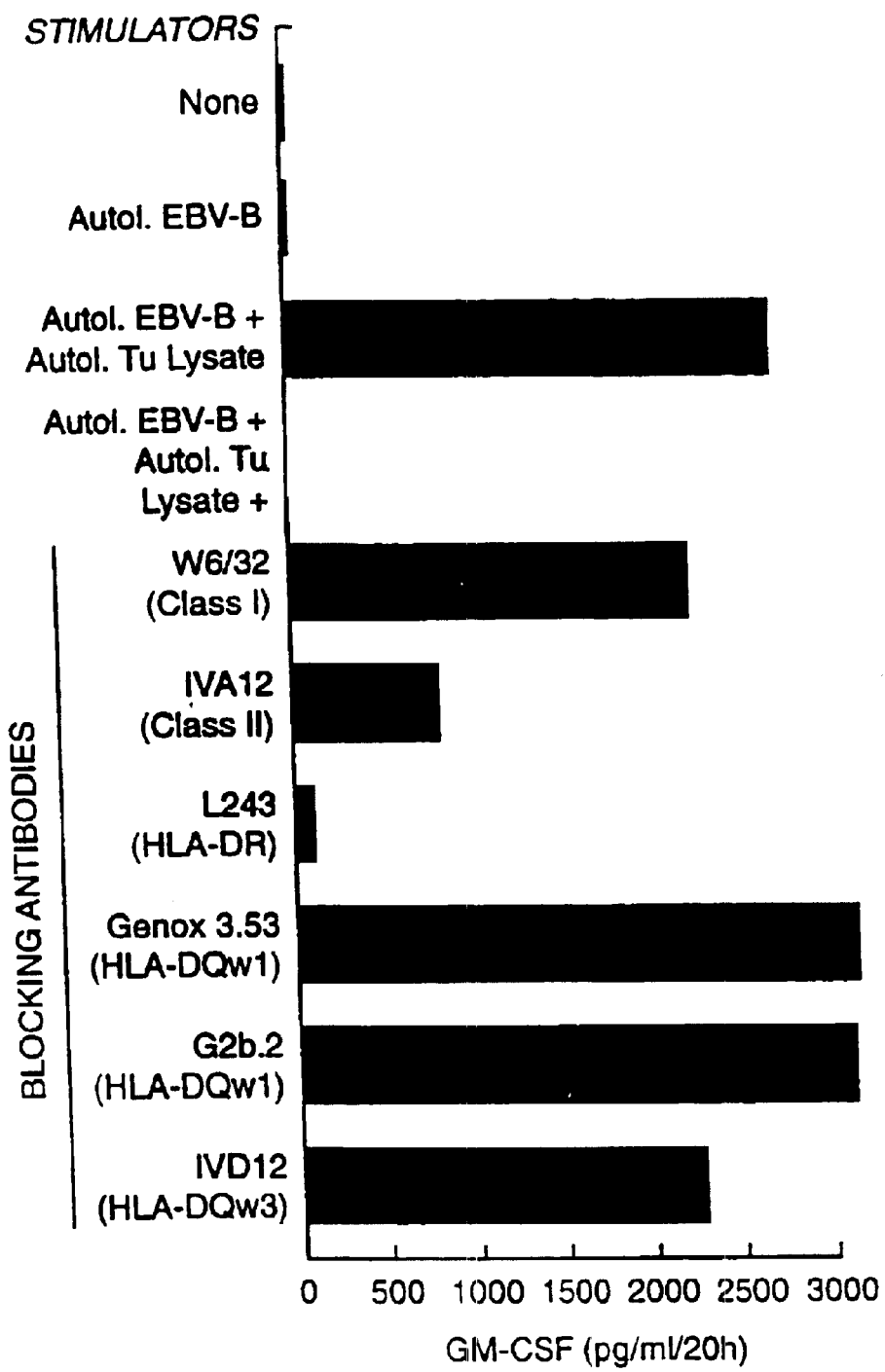
FIG. 1 shows that the response of CD4+ tumor infiltrating lymphocytes (TIL) from patient number 1088 to autologous melanoma cells is HLA-DR restricted. TIL (1×10$^6$/ml) were cultured in the presence of autologous Epstein Barr Virus (EBV)-B cells (1×10$^6$/ml) alone, or B cells pulsed with a lysate of autologous cultured melanoma cells (7×10$^5$ cell equivalents/ml). Secretion of GM-CSF (granulocyte/macrophage-colony-stimulating factor) following autologous tumor stimulation was significantly inhibited by the monoclonal antibody (mAb) L243 (anti-HLA-DR) and IVA12 (anti-HLA-DR,-DP,-DQ).

Major Histocompatibility Complex (MHC) is a generic designation meant to encompass the histo-compatibility antigen systems described in different species, including the human leucocyte antigens (HLA).

The term melanoma includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, and presentation on a cell, or carcinogenic agents. The aforementioned melanomas can be diagnosed, assessed or treated by methods described in the present application.

Immunogenic peptide includes, but is not limited to, an antigenic peptide capable of causing or stimulating a cellular or humoral immune response. Such peptides may also be reactive with antibodies.

This invention provides MHC-Class II restricted melanoma antigens. Such antigens may be the complete protein encoded by a gene, or portions thereof or polypeptides or peptides derived from a protein sequence. Such antigens may be expressed in normal or disease tissues. By way of example, Class II restricted melanoma antigens may be derived from the tyrosinase amino acid sequences. Examples of immunogenic tyrosinase sequences that may be used include, but are not limited to, GenBank accession numbers J03581, U01873, Y00819, and M27160, (Kwon, et al., (1987) *PNAS* 84:7473–7477; Brichard, V. et al., (1993) *J. Exp. Med.* 178:489–495; Bouchard, B. et al. (1989) *J. Exp. Med.* 169:2029–2042; and Shibihara, S. et al., (1988) *J. Exp. Med.* 156:403–414; all herein incorporated by reference). The Class II restricted melanoma antigen may comprise the entire tyrosinase sequence or portions thereof. Examples of immunogenic tyrosinase peptides recognized by CD4+ T cells include, but are not limited to, QNILLSNAPLGPQFP (Ty 56-70), (SEQ ID NO: 1) NILLSNAPLGPQFP (Ty 57-70) (SEQ ID NO: 2), DYSYLQDSDPDSFQD (Ty 448-462) (SEQ ID NO: 6), YSYLQDSDPDSFQD (TY 449-462) (SEQ ID NO: 13), and SYLQDSDPDSFQD (Ty 450-462) (SEQ ID NO: 14) (Peptides are presented in single letter code). Also intended to be encompassed by this invention are proteins or polypeptides comprising these immunogenic peptide sequences. Persons of ordinary skill in the art will recognize that these peptides could be shortened to a minimal MHC Class II binding core of 9 or 10 amino acids by truncating the amino and/or carboxy termini of these peptides or one could lengthen these peptides by adding flanking sequences at either the carboxy or amino terminus of the peptides or at both termini of the peptide. By way of example, such a peptide may range in size from about 9 amino acids to about 34 amino acids.

This invention further includes analogs of these immunogenic peptides derived from the tyrosinase amino acid sequence. The term analog includes any peptide which displays the functional aspects of these immunogenic peptides. The term analog also includes conservative substitution or chemical derivative of the peptides as described above. These peptides may be synthetically or recombinantly produced by conventional methodology.

The term "analog" includes any polypeptide having an amino acid residue sequence substantially identical to the sequences described herein in which one or more residues have been conservatively substituted with a functionally similar residue and which displays the functional aspects of the peptides as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Proteins, polypeptides or proteins of the present invention also include any polypeptide having one or more additions and/or deletions or residues relative to the sequence of a polypeptide or peptide whose sequence are described herein, so long as the requisite activity is maintained.

Figure 11:
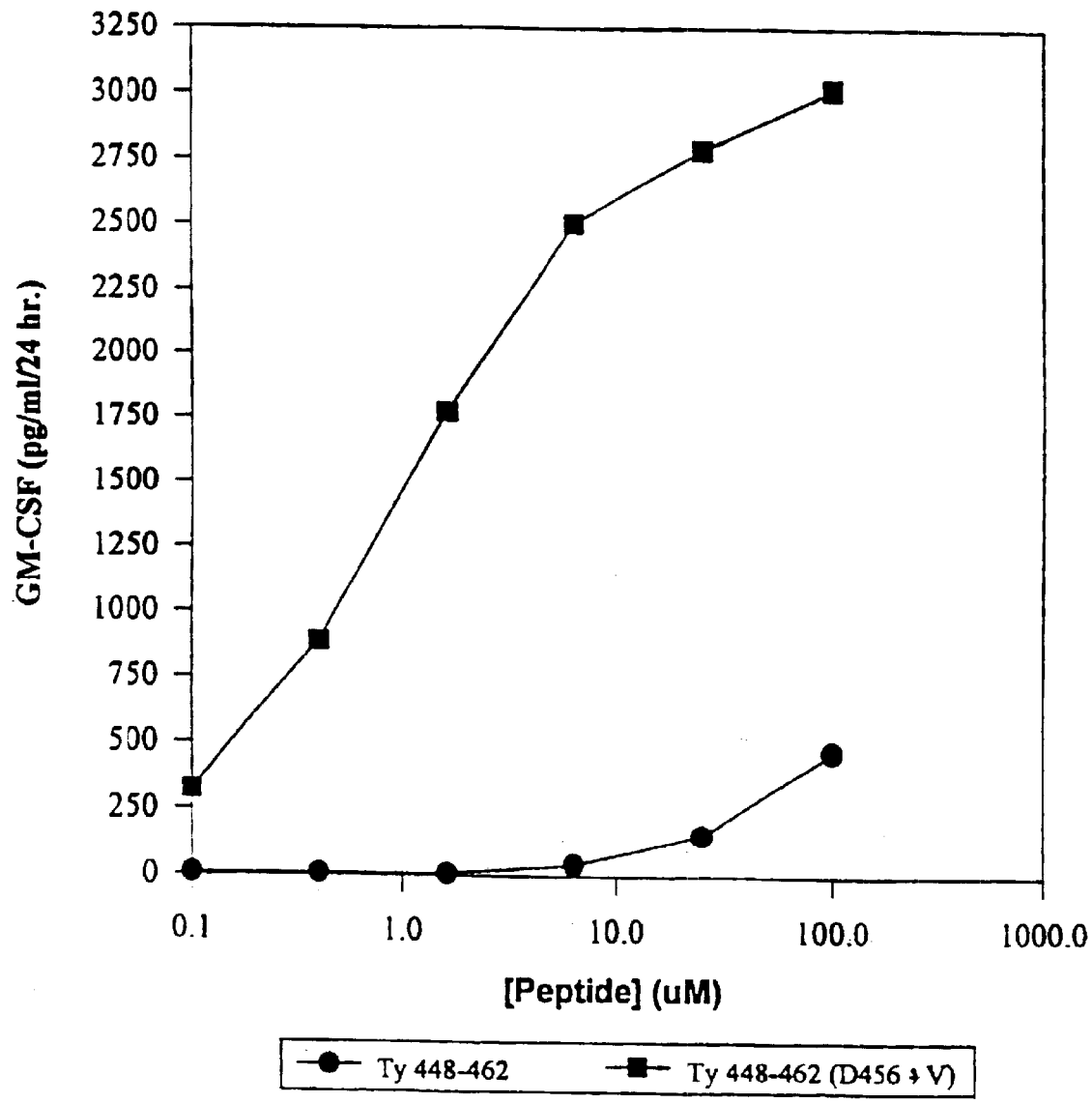
FIG. 11 shows the P6 anchor position for Ty 448-462 is D456. This was presumed, based on identifying Y451 as the P1 anchor. D is not an optimal residue in this position, and a valine substitution led to markedly enhanced CD4+ T cell recognition. When two favorable modifications of Ty 448-462 were combined in a single modified peptide (Ty 450-462, D456→V), recognition was enhanced even more (see FIG. 12).

In yet another embodiment of this invention, Class II restricted peptides derived from a tyrosinase sequence are modified to increase immunogenicity by enhancing the binding of the peptide to the MHC Class II molecule with which the peptide is associated when presented to CD4+ T cells, or by enhancing binding of the peptide to the T cell receptor of the CD4+ T cells. By way of example, modifications may include the substitution, deletion or addition, of one or more amino acids within the peptide sequence, or insertion of amino acids within the given peptide sequence or derivitization of existing amino acids within the given peptide sequence or mutation of the amino acids within the given peptide sequence. Examples of modified QNILLSNAPLGPQFP (Ty 56-70 (SEQ ID NO: 1)) peptides include, but are not limited to, QNILLSNAPVGPQFP (L65→V (SEQ ID NO: 3)), QNILLSNVPVGPQFP (A63→V and L65→V (SEQ ID NO: 4)), and QNILLSNVPLGPQFP (A63→V (SEQ ID NO: 5)) (See FIG. 6). Examples of modified DYSYLQDSDPDSFQD (Ty 448-462 (SEQ ID NO: 6)) peptides include, but are not limited to DYSYLQDSDPDSSQD (F460→S (SEQ ID NO: 7)), DQSYLQDSDPDSFQD (Y449→Q (SEQ ID NO: 8)), DFSYLQDSDPDSFQD (Y449→F (SEQ ID NO: 9)), DYSFLQDSDPDSFQD (Y451→F (SEQ ID NO: 10)), DYSYLQDSVPDSFQD (D456→V (SEQ ID NO: 11)), and SYLQDSVPDSFQD (Ty450-462, D456→V SEQ ID NO: 12)) (see FIGS. 9 and 11).

Preferably the modifications are performed within the Class II core binding of the tyrosinase peptides. In a preferred modification at least one amino acid is substituted or replaced in the given binding core of the immunogenic peptide sequence. Any amino acid composing the given binding core of the immunogenic peptide sequence may be modified in accordance with this invention. Any amino acid may be used to substitute or replace a given amino acid within the binding core of the immunogenic peptide sequence. Modification may occur at any amino acid position within the binding core of an immunogenic tyrosinase peptide. Modified peptides is intended to include any modified peptide exhibiting enhanced binding with the MHC Class II molecule with which it is associated when presented to the CD4+ T cell. Also intended to be encompassed by this invention are proteins or polypeptides comprising or including these peptide sequences. By way of example such proteins or polypeptides may have additional sequences such as flanking sequences either at the carboxy or amino terminus of the peptide or both.

By way of example, the Class II restricted tyrosinase antigens may be recognized by CD4+ T cells in the context of HLA-DR, in particular HLA-DRB1*0401. The core binding sequence of a Class II restricted antigen is about 9 amino acids in length. Preferably for enhanced binding of the peptide to HLA-DRB1*0401 the first position in the core amino acid sequence is an aromatic or aliphatic hydrophobic amino acid. The sixth position may be any hydrophobic amino acid such as, but not limited to, leucine, isoleucine, valine, methionine, or a hydroxyl amino acid, such as serine or threonine (Sette, A. et al (1993) *J. Immunol.* 151, 3163–3170; Rammensee, H. G. et al (1995) *Immunogenetics* 41:178–228, both herein incorporated by reference).

The fourth, seventh and ninth positions of the 9 amino acid binding core sequence of the immunogenic peptide may also be substituted or replaced. Examples of amino acids that may be used at the fourth position of the peptide include, but are not limited to, any hydrophobic amino acid or aspartic or glutamic acid. The seventh position may be any polar, charged or aliphatic amino acid. Examples of amino acids that may be used include but are not limited to aspartic acid, alanine, serine, valine, histidine, proline, asparagine, methionine, threonine, leucine and isoleucine. The ninth position of the peptide may be any polar or aliphatic amino acid. Examples of such amino acids include but are not limited to alanine, serine, glutamine, glycine, leucine, valine, and threonine.

Examples of Class II restricted tyrosinase peptides whose core sequence may be modified in accordance with the present embodiment include, but is not limited to QNILLSNAPLGPQFP (Ty 56-70) (SEQ ID NO: 1), NILLSNAPLGPQFP (Ty 57-70) (SEQ ID NO: 2), DYSYLQDSDPDSFQD (Ty 448-462) (SEQ ID NO: 6), YSYLQDSDPDSFQD (Ty 449-462) (SEQ ID NO: 13), and SYLQDSDPDSFQD (Ty 450-462) (SEQ ID NO: 14). Examples of modified tyrosinase peptides whose core binding sequence may further be modified include, but is not limited to, QNILLSNAPVGPQFP (Ty56-70, L65→V) (SEQ ID NO: 3), QNILLSNVPVGPQFP (Ty 56-70, A63→V and L65→V (SEQ ID NO: 4)), QNILLSNVPLGPQFP (TY 56-70, A63→V (SEQ ID NO: 5)), DYSYLQDSDPDSSQD (Ty 448-462, F460→S (SEQ ID NO: 7)), DQSYLQDSDPDSFQD (Ty 448-462, Y449-Q (SEQ ID NO: 8)), DFSYLQDSDPDSFQD (Ty 448-462, Y449→F (SEQ ID NO: 9)), DYSFLQDSDPDSFQD (Ty 448-462, Y451→F (SEQ ID NO: 10)), DYSYLQDSVPDSFQD (Ty 448-462, D456→V (SEQ ID NO: 11)), and SYLQDSVPDSFQD (Ty450-462, D456→V (SEQ ID NO: 12)).

By way of example modified Class II-restricted tyrosinase peptides derived from the tyrosinase sequence may have a binding core sequence according to the formula $X_1LLX_2NX_3X_4LX_5$ (SEQ ID NO: 15), or $X_1LQX_2SX_3X_4DX_5$ (SEQ ID NO: 16), wherein:

$X_1$ may be any hydrophobic amino acid, either aromatic or aliphatic. Examples of amino acids that may be used include, but are not limited to, leucine, isoleucine, methionine, valine, tryptophan, phenylalanine, or tyrosine. The $X_1$ position corresponds to Ty 58 in peptide Ty56-70, or Ty 451 in peptide Ty 448-462.

$X_2$ may be any hydrophobic amino acid, or aspartic acid or glutamic acid. Examples of amino acids that may be used include, but are not limited to, phenylalanine, tryptophan, leucine, isoleucine, valine, alanine, aspartic acid or glutamic acid.

$X_3$ may be any hydrophobic amino acid, or hydroxyl amino acids. Examples of amino acids that may be used include, but are not limited to, leucine, isoleucine, methionine, valine, serine or threonine.

$X_4$ may be any polar, charged or aliphatic amino acid. Examples of amino acids that may be used include, but are not limited to, aspartic acid, alanine, serine, valine, histidine, proline, asparagine, methionine, threonine, leucine, and isoleucine.

$X_5$ may be any polar, or aliphatic amino acid. By way of example amino acids that may be used on this position include, but are not limited to, alanine, serine, glutamine, glycine, leucine, valine, and threonine.

This invention further includes analogs of these modified peptides derived from the tyrosinase sequence. The term analog is intended to include any peptide which displays the functional aspects of these modified peptides as described above. These modified peptides may be synthetically or recombinantly produced by conventional methods. Also intended to be encompassed by this invention are proteins or polypeptides including these peptide sequences. By way of example such proteins or polypeptides may have additional flanking sequences at either the carboxy or amino terminus of the peptide or at both termini or may be truncated to a minimal 9 amino acid MHC Class II binding core.

This invention also relates to nucleic acid encoding the Class II restricted immunogenic tyrosinase peptides or modified peptides of this invention. It is, however, understood by one skilled in the art that due to the degeneracy of the genetic code variations in nucleic acid sequences will still result in a DNA sequence capable of encoding antigens described herein. Such DNA sequences are therefore functionally equivalent to the sequences intended to be encompassed by the invention. Allelic variations in a given species of the nucleic acid sequence encompassed by this invention are also intended to be encompassed by the present invention. By way of example nucleic acid sequences encoding the tyrosinase or modified tyrosinase peptides QNILLSNAPLGPQFP (Ty 56-70) (SEQ ID NO: 1), NILLSNAPLGPQFP (Ty 57-70) (SEQ ID NO: 2), DYSYLQDSDPDSFQD (Ty 448-462) (SEQ ID NO: 6), YSYLQDSDPDSFQD (Ty 449-462) (SEQ ID NO: 13), SYLQDSDPDSFQD (Ty 450-462) (SEQ ID NO: 14), QNILLSNAPVGPQFP (Ty 56-70, L65 →V) (SEQ ID NO: 3), QNILLSNVPVGPQFP (Ty 56-70, A63→V and L65→V) (SEQ ID NO: 4), QNILLSNVPLGPQFP (Ty 56-70, A63→V) (SEQ ID NO: 5), DYSYLQDSDPDSSQD (Ty 448-462, F460→S) (SEQ ID NO: 7), DQSYLQDSDPDSFQD (Ty 448-462, Y449→Q) (SEQ ID NO: 8), DFSYLQDSDPDSFQD (Ty 448-462, Y449→F) (SEQ ID NO: 9), DYSFLQDSDPDSFQD (Ty 448-462, Y451→F) (SEQ ID NO: 10), DYSYLQDSVPDSFQD (Ty-448-462, D456→V) (SEQ ID NO: 11), and SYLQDSVPDSFQD (Ty450-462, D456→V) (SEQ ID NO: 12), or analogs thereof are intended to be encompassed by this invention.

This invention also provides a recombinant DNA molecule comprising all or part of the nucleic acid sequence encoding a Class II melanoma antigen and a vector. Expression vectors suitable for use in the present invention comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology", John Wiley and Sons, New York, N.Y.) or are commercially available.

Another aspect of this invention relates to a host organism into which a recombinant expression vector containing all or part of the nucleic acid sequence encoding for a Class II melanoma antigens has been inserted. The host cells transformed with the nucleic acid sequences encompassed by this invention include eukaryotes, such as animal, plant, insect and yeast cells and prokaryotes, such as $E.\ coli$. The means by which the vector carrying the gene may be introduced into the cell include, but are not limited to, microinjection, electroporation, transduction, or transfection using DEAE-dextran, lipofection, calcium phosphate or other procedures known to one skilled in the art (Sambrook et al. (1989) in "Molecular Cloning. A Laboratory Manual", Cold Spring Harbor Press, Plainview, N.Y.).

In a preferred embodiment, eukaryotic expression vectors that function in eukaryotic cells are used. Examples of such vectors include, but are not limited to, retroviral vectors, vaccinia virus vectors, adenovirus vectors, herpes virus vector, fowl pox virus vector, plasmids, such as pCDNA3 (Invitrogen, San Diego, Calif.) or the baculovirus transfer vectors. Preferred eukaryotic cell lines include, but are not limited to, COS cells, CHO cells, HeLa cells, NIH/3T3 cells, 293 cells (ATCC# CRL1573), T2 cells, dendritic cells, monocytes or Epstein-Barr Virus transformed B cells. In a preferred embodiment the recombinant protein expression vector is introduced into mammalian cells, such as NIH/3T3, COS-7, CHO, 293 cells (ATCC #CRL 1573), T2 cells, dendritic cells, or monocytes to ensure proper processing and modification of the protein.

The recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the tyrosinase protein (Ausubel et. al., (1987) in "Current Protocols in Molecular Biology" John Wiley and Sons, New York, N.Y.).

This invention further includes an antibody or antibodies reactive with the Class II restricted melanoma antigens described. The antibodies may be monoclonal and polyclonal and are made by conventional methods known to those skilled in the art. In addition, the protein or nucleic acid sequences of the Class II restricted melanoma antigens described herein, may be used diagnostically to screen for the presence, absence or alteration in expression of these antigens using immunoassays or nucleic acid probes.

The Class II restricted melanoma antigens of this invention, or analogs thereof may be used as a vaccine either prophylactically or therapeutically. When provided prophylactically the vaccine is provided in advance of any evidence of melanoma. The prophylactic administration of the Class II restricted melanoma antigen vaccine should serve to prevent or attenuate melanoma in a mammal. In a preferred embodiment mammals, preferably human, at high risk for melanoma are prophylactically treated with the vaccines of this invention. Examples of such mammals include, but are not limited to, humans with a family history of melanoma, humans with a history of atypical moles, humans with a history of FAM-M syndrome or humans afflicted with melanoma previously resected and therefore at risk for reoccurrence. When provided therapeutically, the vaccine is provided to enhance the patient's own immune response to the tumor antigen present on the melanoma or metastatic melanoma. The vaccine, which acts as an immunogen, may be a cell, cell lysate from cells transfected with a recombinant expression vector, cell lysates from cells transfected with a recombinant expression vector encoding for the Class II restricted melanoma antigen, or a culture supernatant containing the expressed protein. Alternatively, the immunogen is a partially or substantially purified recombinant protein, peptide or analog thereof encoding for a Class II restricted melanoma antigen. The proteins or peptides may be conjugated with lipoprotein or administered in liposomal form or with adjuvant using conventional methodologies. Examples of Class II restricted tyrosinase peptides or modified tyrosinase peptides that may be used include but are not limited to QNILLSNAPLGPQFP (Ty 56-70) (SEQ ID NO: 1), NILLSNAPLGPQFP (Ty 57-70) (SEQ ID NO: 2), DYSYLQDSDPDSFQD (Ty 448-462) (SEQ ID NO: 6), YSYLQDSDPDSFQD (Ty 449-462) (SEQ ID NO: 13), SYLQDSDPDSFQD (Ty 450-462) (SEQ ID NO: 14), QNILLSNAPVGPQFP (Ty 56-70, L65→V) (SEQ ID NO: 3), QNILLSNVPVGPQFP (Ty 56-70, A63→V and L65→V) (SEQ ID NO: 4), QNILLSNVPLGPQFP (Ty 56-70, A63→V) (SEQ ID NO: 5), DYSYLQDSDPDSSQD (Ty 448-462, F460→S) (SEQ ID NO: 7), DQSYLQDSDP-DSFQD (Ty 448-462, Y449→Q) (SEQ ID NO: 8), DFSYLQDSDPDSFQD (Ty 448-462, Y449→F) (SEQ ID NO: 9), DYSFLQDSDPDSFQD (Ty 448-462, Y451→F) (SEQ ID NO: 10), DYSYLQDSVPDSFQD (Ty 448-462, D456→V) (SEQ ID NO: 11), and SYLQDSVPDSFQD (Ty450-462, D456→V) (SEQ ID NO: 12), or analogs thereof. The tyrosinase protein or tyrosinase peptides having the modified binding core sequences described herein may also be used.

While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of about 0.11 about 10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of about 0.1 to about 3.0 osmoles, preferably in the range of about 0.8 to about 1.2. The pH of the aqueous solution is adjusted to be within the range of about 5.0 to about 9.0, preferably within the range of 6–8. In formulating the immunogen of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the tyrosinase protein, peptides and analogs thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The proteins of the present invention may be supplied in the form of a kit, alone, or in the form of a pharmaceutical composition as described above.

Vaccination can be conducted by conventional methods. For example, the immunogen can be used in a suitable diluent such as saline or water, or complete or incomplete adjuvants. Further, the immunogen may or may not be bound to a carrier to make the protein immunogenic or enhance the protein's immunogenecity. Examples of such carrier molecules include but are not limited to bovine serum albumin (BSA), keyhole limpet hemocyanin (KLH), tetanus toxoid, and the like. The immunogen also may be coupled with lipoproteins or administered in liposomal form or with adjuvants. The immunogen can be administered by any route appropriate for antibody production such as intravenous, intraperitoneal, intramuscular, subcutaneous, and the like. The immunogen may be administered once or at periodic intervals until a significant titer of $CD4^+$ or $CD8^+$ T cell or antibodies directed against the Class II restricted melanoma antigen is obtained. The presence of cells may be assessed by measuring cytokine secretion in response to antigen-presenting cells pulsed with the immunogen. The antibody may be detected in the serum using conventional immunoassays.

The administration of the vaccine or immunogen of the present invention may be for either a prophylactic or therapeutic purpose. When provided prophylactically, the immunogen is provided in advance of any evidence or in advance of any symptom due to melanoma, or in patients rendered free of disease by conventional therapies but at significant risk for recurrence. The prophylactic administration of the immunogen serves to prevent or attenuate melanoma in a mammal. When provided therapeutically, the immunogen is provided at (or after) the onset of the disease or at the onset of any symptom of the disease. The therapeutic administration of the immunogen serves to attenuate the disease.

By way of example, a vaccine prepared using recombinant expression vectors may be used. To provide a vaccine to an individual a genetic sequence which encodes for all or part of the Class II restricted melanoma antigen is inserted into an expression vector, as described above, and introduced into the mammal to be immunized. Examples of vectors that may be used in the aforementioned vaccines include, but are not limited to, defective retroviral vectors, adenoviral vectors, vaccinia viral vectors, fowl pox viral vectors, or other viral vectors (Mulligan, R. C., (1993) *Science* 260:926–932). The viral vectors carrying the nucleic sequence can be introduced into a mammal either prior to any evidence of melanoma or to mediate regression of the disease in a mammal afflicted with melanoma. Examples of methods for administering the viral vector into the mammals include, but are not limited to, exposure of cells to the virus ex vivo, or injection of the retrovirus or a producer cell line of the virus into the affected tissue or intravenous administration of the virus. Alternatively the viral vector carrying all or part of the tyrosinase nucleic acid sequence encoding the Class II restricted melanoma antigen may be administered locally by direct injection into the melanoma lesion or topical application in a pharmaceutically acceptable carrier. Examples of nucleic acid sequences that may be used include, but are not limited to, nucleic acid sequence encoding the Class II tyrosinase restricted peptides or modified peptides QNILLSNAPLGPQFP (Ty 56-70) (SEQ ID NO: 1), NILLSNAPLGPQFP (Ty 57-70) (SEQ ID NO: 2), DYSYLQDSDPDSFQD (Ty 448-462) (SEQ ID NO: 6), YSYLQDSDPDSFQD (Ty 449-462) (SEQ ID NO: 13), SYLQDSDPDSFQD (Ty 450-462) (SEQ ID NO: 14), QNILLSNAPVGPQFP (Ty 56-70, L65→V) (SEQ ID NO: 3), QNILLSNVPVGPQFP (Ty 56-70, A63→V and L65→V) (SEQ ID NO: 4), QNILLSNVPLGPQFP (Ty 56-70, A63→V) (SEQ ID NO 5), DYSYLQDSDPDSSQD (Ty 448-462, F460→S) (SEQ ID NO: 7) DQSYLQDSDPDSFQD (Ty 448-462, Y449-Q) (SEQ ID NO: 8), DSFSYLQDSDPDSFQD (Ty 448-462, Y449→F) (SEQ ID NO: 9), DYSFLQDSDPDSFQD (Ty 448-462, Y451→F) (SEQ ID NO: 10), DYSYLQDSVPDSFQD (Ty 448-462, D456→V) (SEQ ID NO: 11), and SYLQDSVPDSFQD (Ty450-462, D456→V) (SEQ ID NO: 12), or analogs thereof. In addition, nucleic acid sequences encoding tyrosinase peptides comprising the modified core binding sequences described herein may also be incorporated into recombinant vectors. The quantity of viral vector, carrying the nucleic acid sequence encoding for the Class II restricted melanoma antigen, to be administered is based on the titer of virus particles. By way of example, a range of the immunogen to be administered may be about $10^6$ to about $10^{11}$ virus particles per mammal, preferably a human. After immunization the efficacy of the vaccine can be assessed by production of antibodies or immune cells that recognize the antigen, as assessed by specific cytokine production or by tumor regression. One skilled in the art would know the conventional methods to assess the aforementioned parameters. If the mammal to be immunized is already afflicted with melanoma or metastatic melanoma the vaccine can be administered in conjunction with other therapeutic treatments. Examples of other therapeutic treatment includes, but are not limited to, adoptive T cell immunotherapy, coadministration of cytokines or other therapeutic drugs for melanoma.

Alternatively all or parts thereof of a substantially or partially purified tyrosinase protein corresponding to the Class II restricted melanoma antigen or polypeptides or peptides may be administered as a vaccine in a pharmaceutically acceptable carrier. By way of example, ranges of protein polypeptides or peptides to be administered may be 0.001 to about 100 mg per patient, preferred doses are about 0.01 to about 10 mg per patient. In a preferred embodiment, tyrosinase Class II restricted peptide melanoma antigens or analogs thereof or modified tyrosinase peptides are administered therapeutically or prophylactically to a mammal in need of such treatment. By way of example, doses may be about 0.001 mg to about 100 mg, preferred doses are about 0.01 mg to about 10 mg. The peptide may be synthetically or recombinantly produced. Immunization may be repeated as necessary, until a sufficient titer of anti-immunogen antibody or reactive CD4$^+$ or CD8$^+$ T cells has been obtained.

In yet another alternative embodiment a viral vector, such as a retroviral vector, can be introduced into mammalian cells. Examples of mammalian cells into which the retroviral vector can be introduced include, but are not limited to, primary mammalian cultures or continuous mammalian cultures, COS cells, NIH3T3, or 293 cells (ATTC #CRL 1573), B cell, dendritic or monocytic cell cultures. The means by which the vector carrying the gene may be introduced into a cell includes, but is not limited to, microinjection, electroporation, transfection or transfection using DEAE dextran, lipofection, calcium phosphate or other procedures known to one skilled in the art (Sambrook et al. (eds) (1989) in "Molecular Cloning. A Laboratory Manual", Cold Spring Harbor Press, Plainview, N.Y.). The mammalian cells expressing the Class II restricted melanoma antigen can be administered to mammals and serve as a vaccine or immunogen. Examples of how the cells expressing Class II restricted melanoma antigens can be administered include, but is not limited to, subcutaneous, intravenous, intraperitoneal or intralesional. In a preferred embodiment, the nucleic acid sequence corresponding to Class II restricted peptides or modified tyrosinase peptides is inserted into expression vector and introduced into the mammalian cells. By way of example, the peptides that may be used include, but are not limited to, QNILLSNAPLGPQFP (Ty 56-70) (SEQ ID NO: 1), NILLSNAPLGPQFP (Ty 57-70) (SEQ ID NO: 2), DYSYLQDSDPDSFQD (Ty 448-462) (SEQ ID NO: 6), YSYLQDSDPDSFQD (Ty 449-462) (SEQ ID NO: 13), SYLQDSDPDSFQD (Ty 450-462) (SEQ ID NO: 14), QNILLSNAPVGPQFP (Ty 56-70, L65→V) (SEQ ID NO: 3), QNILLSNVPVGPQFP (Ty 56-70, A63→V and L65→V) (SEQ ID NO: 4), QNILLSNVPLGPQFP (Ty 56-70, A63→V) (SEQ ID NO: 5), DYSYLQDSDPDSSQD (F460→S) (SEQ ID NO: 7), DQSYLQDSDPDSFQD (Ty 448-462, Y449→Q) (SEQ ID NO: 8), DFSYLQDSDPDSFQD (Ty 448-462, Y449→F) (SEQ ID NO: 9), DYSFLQDSDPDSFQD (Ty 448-462, Y451→F) (SEQ ID NO: 10), DYSYLQDSVPDSFQD (Ty 448-462, D456→V) (SEQ ID NO: 11), and SYLQDSVPDSFQD (Ty450-462, D456→V) (SEQ ID NO: 12), or analogs thereof. Nucleic acid sequences encoding tyrosinase peptides having the binding core sequences provided may also be used. Conventional methods would be used to evaluate the immune response of the patient to determine the efficiency of the vaccine.

In yet another embodiment of this invention, the Class II restricted tyrosinase protein, peptides or modified peptides or analogs thereof may be exposed to dendritic cells cultured in vitro. The cultured dendritic cells provide a means of producing CD4$^+$ T cell dependent antigens comprised of dendritic cell modified antigen or dendritic cells pulsed with antigen, in which the protein antigen is processed and expressed on the antigen activated dendritic cell. The antigen activated dendritic cells or processed dendritic cell antigens may be used as immunogens for vaccines or for the treatment of melanoma. Alternatively the dendritic cells may present peptide antigens which have been pulsed on externally. The dendritic cells should be exposed to antigen for sufficient time to allow the antigens to bind directly to their surface MHC Class II molecules, or to be internalized and presented on the dendritic cells surface. The resulting dendritic cells or the dendritic cell processed antigens can than be administered to an individual in need of therapy. Such methods are described in Steinman et al. (WO93/208185) and in Bancherereau et al. (EPO Application 0563485A1) which are incorporated herein by reference. Monocytes, B cells, or Langerhans cells may be substituted for dendritic cells.

In yet another embodiment of this invention CD4$^+$ T cells isolated from individuals can be exposed to the Class II restricted melanoma antigen in vitro and then administered to a patient in need of such treatment in a therapeutically effective amount. Examples of where CD4$^+$ T-lymphocytes can be isolated, include but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami, Y. et al. (1989) *J. Immunol.* 142: 2453–3461). The CD4$^+$ T-lymphocytes are cultured by methods known in the art. The lymphocytes are exposed to peptide or protein antigen for part or all of the culture duration, in the presence of antigen presenting cells. In a preferred embodiment the CD4+lymphocytes are exposed to the Class II restricted tyrosinase peptides or any tyrosinase sequence having the core peptide sequences described herein. By way of example, a concentration of about 1 to about 200 micrograms (ug)/ml peptides per $10^7$ cells for all or part of the duration of lymphocyte culture may be used. After being sensitized to the peptide the T-lymphocytes are administered to the mammal in need of such treatment. Examples of how these sensitized CD4+ T cells can be administered to the mammal include but are not limited to, intravenously, intraperitoneally or intralesionally. Parameters that may be assessed to determine the efficacy of these sensitized T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A. et al. (1992) *Human Gene Therapy*, 3: 75–90; Rosenberg, S. A. et al. (1992) *Human Gene Therapy*, 3: 57–73). By way of example the MHC Class II restricted melanoma antigen may be administered in conjunction with GM-CSF to enhance uptake by professional antigen presenting cells in vivo.

In yet another alternative embodiment Class II restricted melanoma antigens may be linked with MHC Class II molecules and administered either prophylactically or therapeutically to mammals. By way of example the tyrosinase peptides or modified peptides described herein may be coupled with an MHC Class II molecule. Such coupling may be covalent, chemical, or genetic. By way of example, tyrosinase peptides may be genetically linked to the Class II β chain, HLA-DRB1*0401, by a flexible peptide linker which allows the peptide to lie in the binding groove for recognition by T cells (Kozono, H et al (1994) *Nature* 369, 151–154, herein incorporated by reference). According to the promiscuous and degenerate nature of peptide binding to MHC Class II molecules, other DRB1 chains may be used as well (Sinigaglia, F. et al (1995) *J. Exp. Med.* 181, 449–451). Such single-chain Class II-MHC-peptide constructs may be used as vaccines, or may be used to raise reactive CD4+ T cells in vitro.

In yet another alternative embodiment, the aforementioned compositions can be used to prepare antibodies to the Class II restricted melanoma antigens. The antibodies can be used directly as anti-melanoma therapeutic agents or as diagnostic reagents. Further, the antibodies can be made even more compatible with the host system by generating "humanized" chimeric antibodies (Morrison J. 1985, *Science* 229:1202 and Oi, et al. *Biotechniques* (1986) 4:214). Such antibodies can be generated by conventional methods.

In yet another embodiment of this invention, multivalent vaccines against one or more melanoma antigens are provided. Such multivalent vaccines may comprise at least one of the Class II restricted melanoma antigens described herein, preferably the tyrosinase immunogenic peptides disclosed herein or combinations thereof, combined with other known melanoma antigens or peptides derived from these antigens. By way of example, MHC Class II restricted tyrosinase peptides may be combined in a vaccine with MHC Class I restricted peptides derived from tyrosinase or other known melanoma associated proteins to create a multivalent vaccine capable of stimulating helper and cytotoxic immune cells. Examples of known melanoma antigens include, but are not limited to, MART-1, gp100, gp75, MAGE-1 and MAGE-3 or immunogeneic peptides derived from these proteins.

In another embodiment, a method is provided for identifying the presence of Class II restricted antigenic proteins or epitopes of proteins, or of identifying new proteins encoding Class II restricted tumor associated antigens, such as, but not limited to, melanoma antigens. By way of example, the genes or nucleic acid sequences encoding Class I restricted melanoma antigens can be screened for the presence of a Class II restricted antigenic portions or epitopes of the protein encoded by these genes. In this embodiment, the method may comprise the steps of: (a) exposing a candidate antigen to antigen presenting cells (APC) for a period of time sufficient to allow the APC to take up and process the antigen; (b) incubating the APC of step (a) with CD4+ T-lymphocytes; and (c) screening for recognition of the APC by the CD4+ T cells (see Example 1).

In step (a) the candidate antigen may be presented to the APC by either stably on transiently expressing the gene for the candidate antigen in a eukaryotic or prokaryotic expression system. The antigen may then be presented to the APC as crude lysates of the cells expressing the canidate antigen or as purified protein products from the candidate antigen expressing cells. Alternatively a plurality of peptides based on the candidate protein amino acid sequence or based on a truncated protein sequence derived from experiments with serial truncations of the candidate gene may be exposed or incubated with the antigen presenting cell. It is preferred that peptides of about 15 to 20 amino acids be used.

Examples of APC that may be used in step (a) include, but are not limited to, antigen presenting cells such as EBV transformed B cell lines (Topalian et al. (1994) *Int. J. Cancer* 58:69–79), monocytes and dendritic cells. Examples of how to assess recognition by the CD4+ T cells incubated with the APC in step (c) include, but are not limited to, $^{51}$CR release cytotoxicity assays (Cerundolo, V. et al. (1990) *Nature* 345:449–452.), cytokine secretion assays such as γ-IFN, GM-CSF or TNF secretion. (Schwartzentruber, D. et al., (1991) *J. of Immunology* 146:3674–3681), or proliferation assays.

Examples of proteins that may be screened for Class II restricted melanoma antigens includes, but are not limited to MART-1 (Kawakami, et al. (1994) *Proc. Natl. Acad. Sci.* 91:3575–3579), p15 (Robbins, P. F. et al (1995) *J. Immunol.* 154:5944–5950), MAGE-1 (VanderBruggen, *Science* 254:1643–1647), gp100 (Kawakami, et al. (1994) 91:6458–6462), gp75 (Wang, R-F et al (1995) *J. Exp. Med.* 181:799–804), and MAGE-3 (Gaugler, et al. (1994), *J. Exp. Med.* 179:921–930); all herein incorporated by reference.)

Alternatively, this method can be used to clone and identify new genes having CD4 recognized tumor antigens. By way of example, a cell expressing an unidentified tumor antigen would be assessed for CD4+ T cell recognition by pulsing lysates of that cell onto antigen presenting cells (EBV-cells, monocytes, dendritic cells, etc.), and measuring cytokine secretion by T cells during coincubation. A DNA library from the tumor or other stimulatory cell would be expressed in a prokaryotic or eukaryotic host cell and screened according to the methods outlined above.

Also intended to be encompassed by this invention are Class II restricted tumor associated antigens, such as melanoma antigens obtained by these methods.

Veterinary uses are also intended to be encompassed by the compositions and therapeutic applications described herein.

All books, articles, and patents referenced herein are incorporated by reference. The following examples illustrate various aspects of the invention and in no way intended to limit the scope thereof.

EXAMPLE I

Human CD4+ Cells Recognize a Shared Melanoma Antigen Encoded by the Tyrosinase Gene Materials and Methods Lymphocyte Cultures and Clones TIL were cultured from enzymatically digested single cell suspensions of solid metastatic melanoma lesions as previously described (Topalian, S. L , et al. (1987) *J. Immunol. Methods.* 102, 127–141), in the presence of recombinant interleukin-2 (rIL-2; 6000 IU/ml (Chiron Corporation, Emeryville, Calif.)), Lymphocyte cultures were passaged in bulk for 4 to 6 weeks, and then CD4+ and CD8+ TIL subsets were purified by positive selection on tissue culture flasks carrying covalently bound anti-CD4 or anti-CD8 monoclonal antibodies (mAb) (Applied Immune Sciences, Menlo, Park, Calif.) (Morecki, S., et al. (1990) *J. Biol. Resp. Modiff.* 9, 463–474). Uncloned CD4+ TIL were tested in bioassays after 45–70 days of culture. CD4+ T cell clones were established from a 35-day bulk TIL 1088 culture which was 52% CD4+. CD4+ T cells were selected and then cloned by limiting dilution in microtiter plates, in the presence of 600 IU/ml IL-2, pooled allogeneic PBL from 3 donor's (total $3 \times 10^4$ cells/well, 3000 rad; 1 rad=0.01Gy), and autologous Epstein Barr Virus (EBV) -B cells (1088-EBV $1 \times 10^4$ cells/well, 10,000 rad) pulsed with a freeze/thaw lysate of autologous tumor (1088-mel). Clones were restimulated weekly with allogeneic peripheral blood lymphocytes (PBL), 1088-EBV, and whole 1088-mel cells ($1 \times 10^3$ cells/well, 30,000 rad). Clones used for bioassays were grown from 0.3 or 1 cell/well dilutions, and tested after 58–155 days of culture.

B Cell Lines

EBV-transformed B cell lines were established from the PBL of melanoma patients using standard techniques (*Current Protocols In Immunology*, Coligan, J. E. et al. (eds) Wiley and Sons, N.Y., N.Y. 7.22.1–7.22.3 (1994) herein incorporated by reference). These lines were maintained as suspension cultures in RPMI+10% FCS.

Tumors and Normal Melanocytes

Melanoma cultures were established from fresh or cryopreserved single cell suspensions of metastatic lesions and maintained as adherent monolayers in RPMI+10% FCS, as described (Topalian, S. L., et al. (1989) *J. Immunol.* 142, 3714–3725). Tumor clones were established by limiting dilution in 96-well flat bottom plates (Costar).

The normal melandcyte cultures FM 707, FM 708, FM 902, FM 906 and FM 907, generated from neonatal foreskin, were a generous gift of Dr. Meenhard Herlyn (Wistar Institute, Philadelphia, Pa; Herlyn, M , et al. (1985) *Cancer Res.* 45, 5670–5676). Cultures were maintained in Melanocyte Growth Medium (MGM, Clonetics, San Diego, Calif.), a basal serum-free medium supplemented with recombinant basic fibroblast growth factor (1 ng/ml), insulin (5 ug/ml), hydrocortisone (0. 5 ug/ml), PMA (10 ng/ml), bovine pituitary extract, gentamicin (50 ug/ml), and amphotericin B (50 ng/ml). Cells were removed from this medium for several days prior to bioassays.

The cultured colon carcinoma CY13 was a gift of Dr. J. Yannelli (NIH, Bethesda, Md.). Colon carcinomas WiDr, LoVo, SW480; breast carcinomas ZR-75-1 and MCF7; and Ewing's sarcomas 6647, RD-ES, and TC-71 were all obtained from the American Type Culture Collection (ATCC, Rockville, Md.) and maintained in RPMI+10% FCS. All cultures tested negative for mycoplasma contamination.

Fresh tumor specimens were prepared from enzymatically dispersed single cell suspensions of solid tumors, including melanomas, colon carcinomas, sarcomas, and lymphomas. They were cryopreserved in 90% FCS+10% DMSO, and were rapidly thawed for immediate use on the day of bioassay.

Antigen Presentation to T Cells by EBV-Transformed B Cells

Optimization of a bioassay for tumor-reactive CD4+ T cells, using EBV-B cells as antigen presenting cells for lysates of whole tumor cells, has been described (Topalian, S. L., et al. (1994) *Int. J. Cancer.* 58:69–79). Assay medium consisted of RPMI+10% AB serum with IL-2 120 IU/ml. Briefly, washed EBV-B cells were cultured at $7–10 \times 10^5$ cells/ml. Tumor antigen was added to B cells in the form of cell lysates: concentrated preparations of washed whole tumor cells were subjected to 3 cycles of rapid freezing and thawing, and cell fragments were added to B cells at $7–10 \times 10^5$ cell equivalents/ml. Tumor-pulsed B cell cultures were maintained at 37° C. for 20–24h, then TIL were added at $4–10 \times 10^5$ cells/ml. Cultures were established in flat-bottom 96-well plates (220 ul/well), 48-well plates (550 ul/well), or 24-well plates (1100 ul/well) depending on the numbers of cells available. As a positive control, TIL were also cultured in plates coated with anti-CD3 mAb (OKT3; Ortho Pharmaceuticals, Raritan, N.J.). Cultures were maintained for an additional 20–24 hours (h), then supernatants were harvested by centrifugation and stored at −80° C. until assayed for the presence of cytokines. Secreted cytokines were measured with ELISA kits purchased from R+D Systems (Minneapolis, MN) for granulocyte-macrophage colony stimulating factor (GM-CSF, detectable concentrations 8-500 pg/ml), tumor necrosis factor alpha (TNF-α, 15–1000 pg/ml), IL-4 (31–2000 pg/ml) and IL-6 (3–300 pg/ml). GM-CSF assays were calibrated with international reference standard 88/646 (NCI-FCRDC, Frederick, Md.). Interferon gamma (IFN-γ) was measured with an ELISA developed with reagents from Biosource International (Camarillo, Calif.) (20–10,000 pg/ml).

The response of TIL to tumor stimulation was considered to be significant when cytokine secretion in response to tumor-pulsed EBV-B cells exceeded the response to EBV-B cells alone by $\geq 3.0$-fold.

Antibody Blocking Studies

To inhibit TIL recognition of tumor-pulsed EBV-B cells, stimulator cells were cultured with preservative-free mAb for 30 min at room temperature before adding TIL, and then cultures were maintained for 24 h at 37° C. in the continued presence of mAb 23 ug/ml. Antibodies directed against HLA determinants included W6/32 (against HLA-A, B, C; $IgG_{2a}$; Sera-Lab, Sussex, England), IVA12 (HLA-DR, DP, DQ;IgG), L243 (HLA-DR;$IgG_{2a}$), Genox 3.53 and G2b.2 (HLA-DQwl;IgG, and $IgG_{2a}$, respectively), and IVD12 (HLA-DQw3;IgG) (all purified from ATCC hybridoma supernatants).

Transfection of COS-7 Cells

Genes cloned into the expression vectors pcDNA3 (Invitrogen, San Diego, Calif.) or pCEV27 (Miki, T., et al. (1991) *Proc. Nat. Acad. Sci. USA* 88, 5167–5171) were transiently transfected into the monkey kidney COS-7 cell line (a gift of Dr. W. Leonard, NIH) using the DEAE dextran method (Seed, B , & Aruffo, A. (1987) *Proc. Natl. Acad. Sci. USA* 84, 3365–3369). EBV-B cells were pulsed with lysates of transfected COS-7 cells for recognition by T cells. The tyrosinase gene was isolated from a cDNA library from the cultured melanoma line 1290A-mel, and its identity was confirmed by partial DNA sequencing which gave a sequence identical to that published by Bouchard (Bouchard, B., et al. (1989) *J. Exp. Med.* 169, 2029–2042).

The tyrosinase (1–3) (comprising exons 1 through 3) gene, also isolated from the 1290A-mel library, lacks the fourth and fifth exons and encodes a truncated product. The gene encoding tyrosinase related protein (gp75) was isolated by screening a cDNA library from 501-mel with a probe constructed based on the published gene sequence (Vijayasaradhi, S., et al. (1990) *J. Exp. Med.* 171, 1375–1380).

Results

CD4$^+$ T cells were purified by positive selection from a heterogeneous population of bulk cultured TIL derived from a metastatic melanoma lesion from patient 1088. Selected cultures were >95% CD4$^+$. Preliminary experiments indicated that these CD4$^+$ T cells secreted cytokines specifically when cocultivated with autologous EBV-B cells (1088-EBV) which had been pulsed with lysates of autologous melanoma cells (1088-mel). TIL secreted large quantities of GM-CSF, and much smaller quantities of TNF-$\alpha$, IL-4, and IFN-$\gamma$ in response to autologous tumor; specific IL-6 secretion was not observed. Thus, GM-CSF secretion was monitored as a measure of T cell recognition in subsequent assays. In 11 separate experiments, CD4$^+$ TIL stimulated with tumor-pulsed EBV-B cells secreted 8- to 138-fold more GM-CSF (median 46-fold) than TIL stimulated with EBV-B cells in the absence of tumor. As shown in FIG. 1, GM-CSF secretion could be abrogated by blocking with the anti-HLA-DR mAb L243 (96% inhibition), suggesting that TIL reactivity was HLA-DR restricted. Significant blocking of cytokine secretion was also observed by the anti-class II framework mAb IVA12 (71% inhibition), but not by isotype-matched mAb directed against a monomorphic MHC class I determinant or against two HLA-DQ determinants (HLA type of patient 1088:HLA-DR 4, 17; HLA-DQw2, 3; HLA-DRw52, 53). Conversely, in the same experiment, cytokine secretion by purified CD8$^+$ TIL 1088 in response to whole autologous melanoma cells (MHC class I$^+$, class II$^-$) was inhibited by the anti-class I mAb W6/32, but not by L243 or IVA12 (data not shown). This experiment was repeated once with similar results. CD8$^+$ TIL 1088 capable of recognizing whole 1088-mel cells failed to react to 1088-EBV cells pulsed with tumor lysate. These data indicate that CD4$^+$ TIL 1088 recognize autologous tumor antigen presented by EBV-B cells in a specific, MHC class II-restricted manner.

Figure 2:
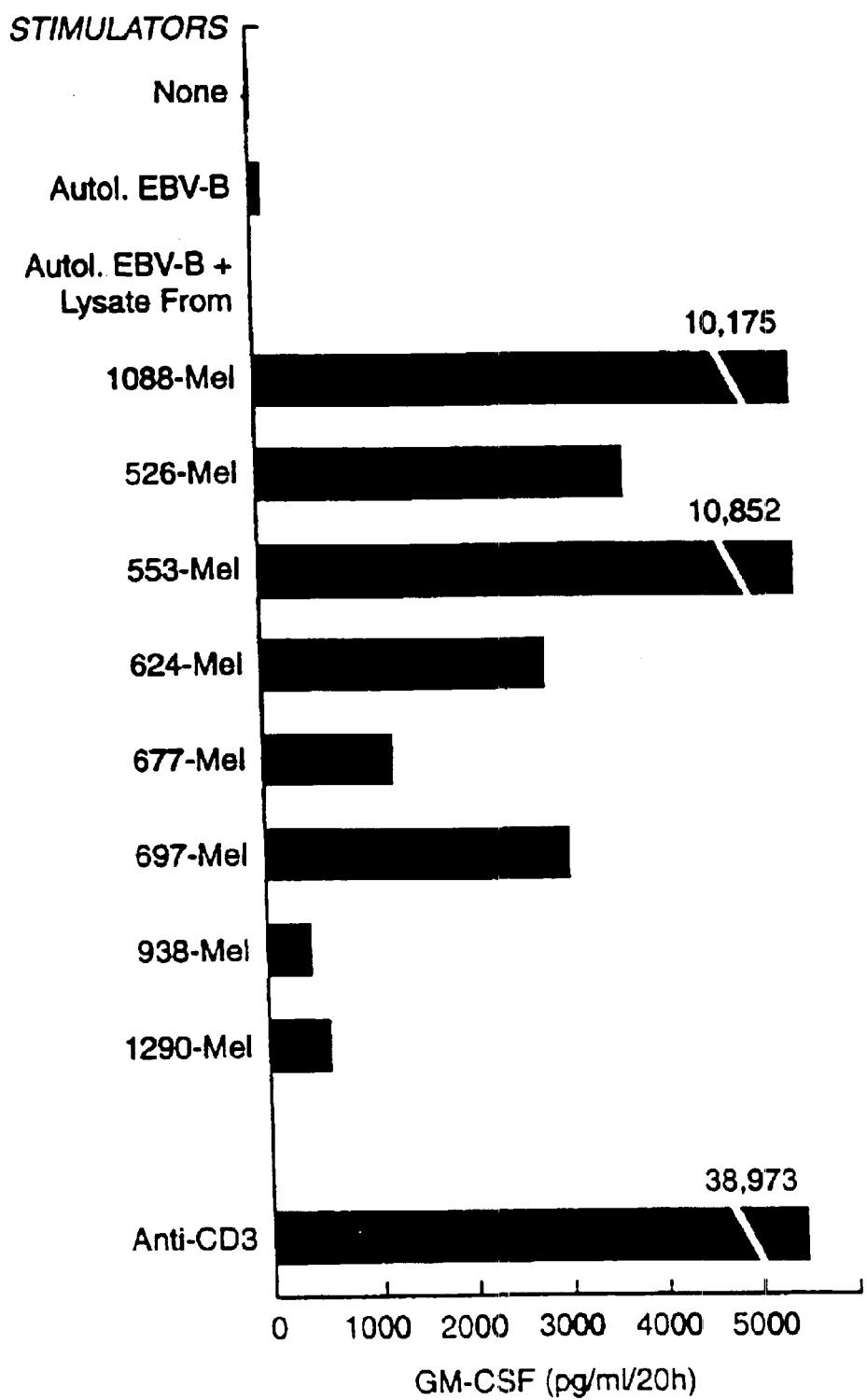
FIG. 2 shows CD4+ TIL 1088 recognize lysates of autologous and allogeneic cultured melanoma lines presented by autologous EBV-B cells, indicating a commonly expressed melanoma antigen. TIL cultured for 58 days in the presence of IL-2 were incubated for 20 hours (h) with tumor-pulsed 1088-EBV. GM-CSF secretion was measured by ELISA. All cells were at 1×10$^6$/ml.

A variety of allogeneic tumors and normal tissues were screened for the presence of Ag recognized by CD4$^+$ TIL 1088. A representative experiment is shown in FIG. 2, in which lysates of the autologous cultured melanoma line as well as all 7 allogeneic melanoma cultures tested were stimulatory. Stimulation indices [SI=GM-CSF secretion by (TIL+EBV-B+cell lysate)/(TIL+EBV-B)] ranged from 4.2 for 938-mel to 104.8 for 553-mel. TIL alone secreted 22 pg/ml GM-CSF, and when cocultivated with unpulsed 1088-EBV secreted 101 pg/ml, as compared to 10,175 pg/ml secreted in the presence of 1088-EBV pulsed with 1088-mel lysate. In separate experiments, a total of 18 fresh or cultured melanomas were screened for recognition, of which 12 were positive (67%), 4 were negative, and 2 equivocal on repeat experiments. Although tumor 624-mel was recognized by TIL 1088 on 5 separate occasions (SI=8.0 to 24.8), only 4 of 6 tumor clones from 624-mel were recognized. Taken together, these results suggest that the Ag recognized by CD4$^+$ TIL 1088 are broadly but not universally expressed in melanoma lesions; alternatively, recognition may reflect relative degrees of antigen expression and the sensitivity of our detection system. Of note, TIL recognized autologous fresh melanoma cells (SI=19.0 and 13.1 in two experiments) as well as tumor cultured from the same lesion (1088-mel), from passages 6 through 48. Thus, the recognized antigen were present in vivo and were not a function of culture artifact; their expression was conserved through almost one year of continuous in vitro culture.

Although TIL recognized a number of allogeneic melanomas on repeat assays, they consistently failed to react with normal cells of nonmelanocyte lineage derived from the same patients. For instance, CD4$^+$ TIL 1088 responded to 1088-EBV pulsed with 1088-mel lysate but not to these same EBV-B cells pulsed with 1088-EBV lysate (SI=35.7 and 1.4, respectively). This experiment was repeated twice with similar results. Also, TIL secreted significant amounts of GM-CSF in response to a lysate of fresh 501B melanoma cells, but not to lysates of EBV-B cells or cultured fibroblasts derived from the same patient (SI=13.4, 2.2, and 1.5 respectively).

Figure 3:
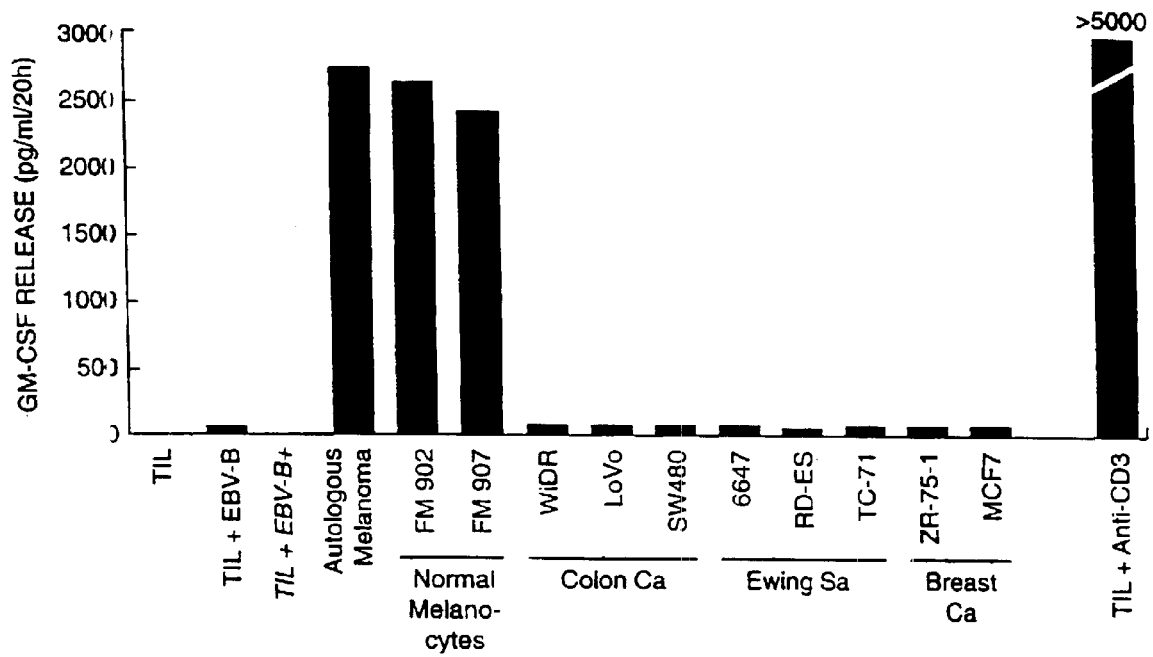
FIG. 3 shows CD4+ TIL 1088 react with melanoma cells and normal melanocytes, but not with tumors of other histologies. TIL secreted significant amounts of GM-CSF when stimulated with autologous EBV-B cells pulsed with lysates of the autologous 1088-mel or normal melanocytes FM 902 and FM 907, but not pulsed with lysates of colon cancers, breast cancers, or Ewing's sarcomas. All cells were 10$^6$ per ml. Ca, cancer; Sa; sarcoma

TIL were tested for recognition of a variety of nonmelanoma tumors, both fresh and cultured. As represented in FIG. 3, TIL failed to recognize lysates from 14 tumors of various histologic types, including colon carcinomas, breast carcinomas, lymphomas, and sarcomas. TIL also failed to react with two Ewing's sarcomas, which share a neuroectodermal embryonic origin with melanomas and were recognized by melanoma-specific CD8$^{30}$ T cells in a previous study (Shamamian, P., et al. (1994) *Cancer Immunol. Immunother.* 39:73–83). However, CD4$^+$ TIL 1088 did recognize all four normal melanocyte lines assayed, on repeated occasions. Measured levels of GM-CSF secretion approached those observed in response to 1088-mel. These results suggested that the Ag recognized by CD4$^+$ TIL 1088 might be specific for the melanocytic lineage.

Two other melanoma patients whose CD4$^+$ TILs recognized lysates of autologous melanoma cells presented by autologous or HLA-matched EBV-B cells had previously been identified (Topalian, S. et al., (1994) *Int. J. Cancer* 58:69–79) by our laboratory. These TILs appeared to be MHC class II-restricted and to recognize antigens unique to autologous melanoma cells, since they failed to react with 15 allogeneic melanomas including 1088-mel or with normal cells including cultured melanocytes. These results suggest the existence of multiple class II-restricted melanoma determinants which are differentially and specifically recognized by CD4$^+$ T cells from these three patients.

TIL cultured in bulk under the conditions described have been shown to be oligoclonal, but not monoclonal cell populations (Belldegrun, A., et al. (1989) *J. Immunol.* 142, 4520–4526; Topalian, S. L., et al. (1990) *J. Immunol.* 144, 4487–4495; Nishimura, M. I., et al. (1993) *J. Cell. Biochem.* 17D, 110. (Abstr.)). To determine whether multiple shared antigens were being recognized by CD4$^+$ TIL 1088, CD4$^+$ T cell clones were raised from these TIL and assayed for target recognition. As shown in Table 1, 4 clones recognized the autologous melanoma as well as multiple allogeneic melanomas and all three normal melanocyte lines tested (FM 902, 906, 907). The target recognition profiles of all 4 clones were remarkably similar and antibody blocking studies suggested that all were HLA-DR restricted. For 2 clones, HLA-DR restriction was confirmed by using allogeneic EBV-B cell lines or macrophages as APC for tumor antigen; only antigen presenting cells sharing the HLA-DR4 molecule were stimulatory. Thus, a single antigenic protein seemed to be present in all of the melanomas recognized by these CD4$^+$ T cell clones, and was shared by normal melanocytes. Further experiments with these and 7 additional CD4$^+$ TIL 1088 clones revealed a homogeneous recognition profile, suggesting the presence of an immunodominant epitope in the 1088 system.

CD4+ TIL 1088 clones were assessed for recognition of melanoma-associated gene products expressed by 1088-mel on Northern blotting and known to contain commonly expressed CD8 epitopes which can be recognized by CTL derived from melanoma patients. The genes encoding the tyrosinase, MART-1, and gp100 proteins (Brichard, V., et al. (1993) *J. Exp. Med.* 178, 489–495; Kawakami, Y., et al. (1994) *Proc. Natl. Acad. Sci. USA.* 91, 3515–3519; Bakker, A. B. H., et al. (1994) *J. Exp. Med.* 179, 1005–1009; Kawakami, Y., et al. (1994) *Proc. Natl. Acad. Sci. USA* 91, 6458–6462) were cloned into plasmid vectors and transiently expressed in monkey kidney COS-7 cells. Lysates of transfected COS-7 cells were pulsed onto 1088-EBV and used to stimulate cytokine secretion from CD4+ T cell clones. Table 2 shows that all 6 T-cell clones tested secreted significant amounts of GM-CSF in response to lysates of tyrosinase-transfected COS-7 cells as well as to lysates from 1088-mel cells. Transfection of COS-7 cells with a truncated tyrosinase gene, or genes encoding the gp75 tyrosinase-related protein, β-galactosidase, or HLA-A2.1 did not confer recognition. As a control, CD8+ T cells from patient 1088 failed to react with any of these stimulator cells. Of note, uncloned CD4+ T cells did not react as strongly as the clones with the tyrosinase gene product. This may reflect the presence of additional epitopes recognized by CD4+ TIL 1088 subpopulations not represented by these clones, as also suggested by some discrepancies in the recognition of allogeneic melanomas by the bulk-cultured TIL compared to the T cell clones (compare FIG. 2 to Table 1). In three additional experiments, CD4+ T cell clones specifically recognized the products of tyrosinase genes isolated from two different patients' melanomas and expressed in two different plasmids, while failing to react with MART-1 or gp100 (not shown). Taken together with previous demonstrations of CD8+ T cell reactivity in melanoma patients against HLA-A2 and HLA-A24 restricted epitopes encoded by the tyrosinase gene (Brichard, et al. (1993) *J. Exp. Med.* 178:489–495; Robbins, P. F. et al. (1994) *Cancer Research* 54:3124–3126), these findings show that a single gene product, tyrosinase, contains epitopes recognized by both CD4+ and CD8+ T lymphocytes. Furthermore, the fact that the CD4+ TIL react to lysates of melanomas as well as normal melanocytes suggests that the recognized epitope is nonmutated.

The importance of CD4+ T cells in the priming and effector phases of the antitumor immune response has been shown in animal models (Greenberg, P. D., et al. (1985) *J. Exp. Med.* 161, 1122–1134; Kern, D. E., et al. (1986) *J. Immunol.* 136, 4303–4310; Ostrand-Rosenberg, S., Roby, C. A., & Clements, V. K. (1991) *J. Immunol.* 147, 2419–2422; Dranoff, G., et al. (1993) *Proc. Natl. Acad. Sci. USA* 90, 3539–3543). Although experimental immunization strategies for patients with melanoma and other cancers currently emphasize shared class I restricted tumor antigens recognized by CD8+ T cells, immunization against both class I and class II restricted epitopes may increase the effectiveness of these approaches.

TABLE 1

CD4+ T cell clones recognize a shared antigen expressed on autologous and allogeneic melanomas and normal melanocytes

| | GM-CSF secretion, †pg/ml per 24 hr (SI‡) | | | |
|---|---|---|---|---|
| Stimulator* | NT9 | 1D6 | 1B7 | 1E7 |
| 1088-mel | 14,581 (504) | 27,992 (384) | 21,497 (169) | 13,767 (101) |
| 1011-mel | 13,626 (471) | 18,937 (260) | 15,882 (125) | 9,292 (68) |
| 553-mel | 2,856 (99) | 11,067 (153) | 9,357 (74) | 4,777 (36) |
| 697-mel | 2,451 (86) | 8,887 (123) | 6,497 (52) | 3,382 (26) |
| 526-mel | 168 (7) | 2,117 (30) | 1,400 (12) | 196 (2) |
| 624-mel | 44 (3) | 1,537 (22) | 1,187 (10) | 98 (2) |
| 1087-mel | 37 (2) | 806 (12) | 675 (6) | 53 (1) |
| 1290B-mel | <8 (1) | 168 (3) | 120 (2) | 33 (1) |
| 938-mel | <8 (1) | 50 (2) | 32 (1) | <8 (1) |
| 1102-mel | <8 (1) | <8 (1) | <8 (1) | <8 (1) |
| 586-mel | <8 (1) | 55 (2) | 18 (1) | <8 (1) |
| 537-mel | <8 (1) | 34 (1) | <8 (1) | <8 (1) |
| 501A-mel | <8 (1) | 24 (1) | <8 (1) | <8 (1) |
| 677-mel | <8 (1) | 22 (1) | <8 (1) | <8 (1) |
| CY13 | <8 (1) | <8 (1) | <8 (1) | <8 (1) |
| 1088-EBV | <8 (1) | <8 (1) | <8 (1) | <8 (1) |
| FM 902 | 5,831 (202) | 12,667 (175) | 10,517 (83) | 6,557 (49) |
| FM 906 | 11,376 (393) | 17,767 (244) | 16,307 (128) | NT |
| FM 907 | 9,401 (325) | 17,382 (239) | 15,202 (120) | NT |

NT, not tested.
*Cell lysates of cultured lines listed were incubated with 1088-EBV cells for 20 hr. In the same experiment, CD8+ TIL 1088 failed to react with these stimulators (data not shown).
†Net secretion = (secretion by TILS with EBV-B plus cell lysate) − (secretion by TILS with EBV-B). All cells were at $4 \times 10^5$ per ml in microtiter plates.
‡Stimulation index. GM-CSF secretion by TIL with EBV-B in the absence of cell lysate ranged from 29 to 138 pg/ml.

TABLE 2

CD4+ T cell clones recognize a product of the tyrosinase gene

GM-CSF secretion, ‡pg/ml per 24 hr

| Stimulator* | Transfected gene† | CD4+ bulk TILs | CD8+ bulk TILs | NT9 | 1D6 | 1B7 | 1E7 | 2G2 | 2F9 |
|---|---|---|---|---|---|---|---|---|---|
| 1088-mel | None | 6169 | 56 | 32,904 | 58,515 | 43,550 | 17,563 | 11,702 | 38,295 |
| COS-7 | Tyrosinase | 123 | <8 | 2,804 | 7,015 | 9,150 | 2,163 | 12,202 | 39,995 |
| COS-7 | Tyrosinase (1–3) | 12 | <8 | <8 | 14 | <8 | <8 | <8 | <8 |
| COS-7 | Tyrosinase-related gp75 | <8 | <8 | <8 | <8 | 46 | <8 | <8 | 37 |
| COS-7 | β-Galactosidase | 8 | <8 | <8 | 16 | 36 | 16 | <8 | <8 |
| COS-7 | HLA-A2.1 | 8 | <8 | <8 | 22 | <8 | <8 | <8 | 12 |

*Cell lysates were cocultivated with 1088-EBV for 20 hr.
554 Genes were expressed in the plasmid vector pcDNA3 except for the tyrosinase-related gp75 gene, which was in pCEV27.
555 Net secretion is defined in footnote † to Table 1. Values to TIL with EBV-B ranged from 10 to 237 pg/ml.

EXAMPLE II

MHC Class II Restricted Tyrosinase Peptides And Modifications Thereof

Materials and Methods

Peptide Synthesis.

Peptides were synthesized by a solid phase method using a peptide synthesizer, and their molecular weights confirmed by mass spectrometry. HA 307-319 and MT(65) 3-13, with high affinities for HLA-DRB1*0401 and B1*0301, respectively, were synthesized for use as inhibitors of tyrosinase peptide binding (Sette, A. et al (1993) *J. Immunol.* 151, 3163–3170; Sidney J. et al (1992) *J. Immunol.* 149, 2634–2640, herein incorporated by reference).

Tumor Cell Lines And Other Cell Lines.

Same as in Example 1

Isolation of CD4+ TIL 1088.

Same as in Example 1.

Assessment of Antigen Recognition by CD4+ TIL 1088.

EBV-B cells were incubated overnight in the presence of peptides, up to 100 μM concentrations. CD4+ T cells were added for an additional 24 hours, and cytokine secretion measured to assess T cell stimulation (see Example 1).

Results.

Two tyrosinase peptides recognized by bulk CD4+ TIL1088 have been identified: Ty 56-70 and Ty 448-462 (FIG. 7). This was done by screening overlapping 15-mers based on a tyrosinase sequence derived from melamona cell line 501-mel, (this sequence is the same as GenBank J03581 sequence but with an R instead of Q at amino acid position 402). These peptides are nonmutated, since their amino acid sequences are identical to a tyrosinase sequence derived from normal human melanocytes (Kwon et. al., *PNAS* (1987) 84:7473–7477; GenBank Accession Number J03581).

Figure 4:
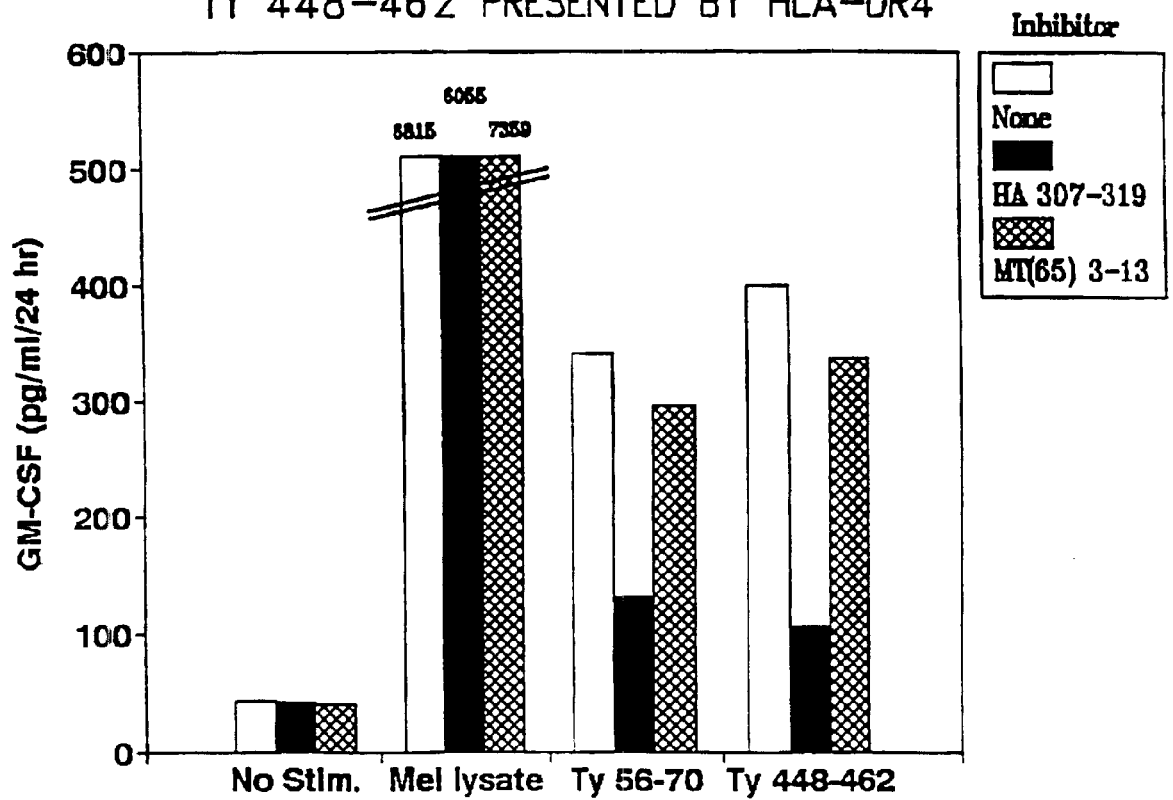
FIG. 4 shows that CD4+ TIL 1088 recognize two different tyrosinase peptides. HLA-DRB1*0401 was identified as the presenting molecule for both Ty 56-70 and Ty 448-462. CD4+ TIL 1088 recognition was assessed by GM-CSF secretion. Peptides HA 307-319 and MT(65) 3-13 were used as inhibitors for B1*0401 and B1*0301, respectively.

CD4+ T cells from patient 1088 had been shown to recognize lysates of autologous and some allogeneic melanoma cell lines expressing tyrosinase, and recognition (measured via cytokine secretion) was HLA-DR-restricted (Example 1; FIGS. 1 and 2). Patient 1088 was heterozygous for DR, expressing HLA-DRB1*0301 and B1*0401. A peptide binding HLA-DRB1*0401 with high affinity, HA 307-319, effectively blocked binding of both the Ty 56-70 and Ty 448-462 peptides to the presenting EBV-B cells derived from patient 1088, leading to decreased T cell recognition (see FIG. 4). A peptide with high affinity for HLA-DRB1*0301, MT(65)3-13, failed to inhibit T cell recognition. Neither HA 307-319 nor MT(65) 3-13 affected T cell recognition of a melanoma lysate, which is internalized by B cells and processed prior to presentation (Topalian *Int. J. Cancer*, 1994 58:69–79). The HLA-restriction of Ty 56-70 and Ty 448-462 was confirmed as HLA-DRB1*0401 by using B cell lines of various HLA genotypes as antigen presenting cells (See FIG. 5).

Figure 8:
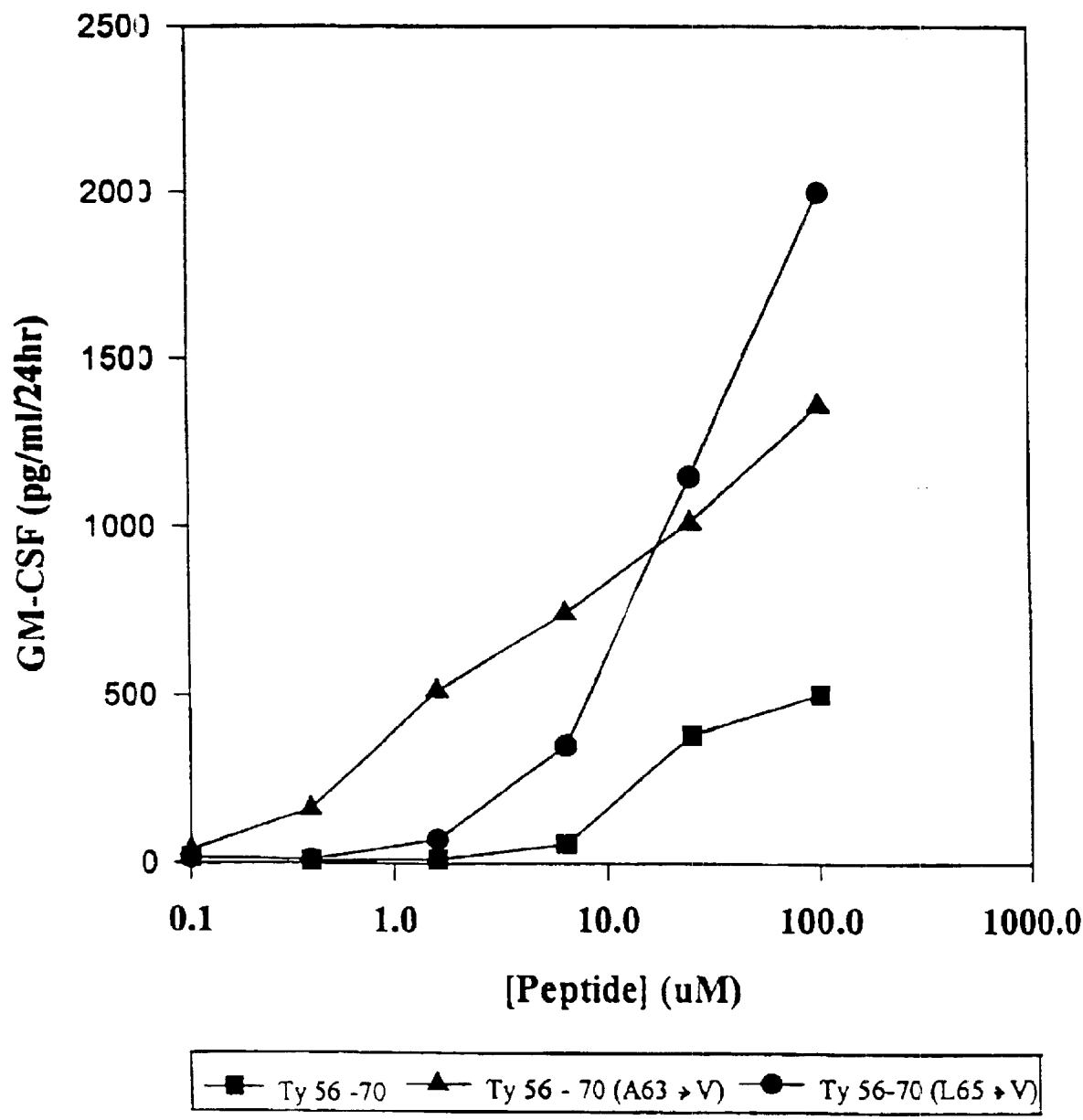
FIG. 8 shows CD4+ 1088 TIL recognize modified tyrosinase 56-70 (Ty 56-70) peptides better than the nonmutated or non-modified peptide. (Background TIL+EBV=118 pg/ml, subtracted.)

In order to make more immunogenic peptides for induction of a CD4+ T cell response, a variety of peptide epitopes were synthesized in which at least one amino acid position was changed based on the binding motifs of peptides presented by HLA-DRB*0401 (Sette, A. et al (1993) *J. Immunol.* 151, 3163–3170; Rammensee, H. G. (1995) *Immunogenetics* 41, 178–228, herein incorporated by reference). The P1 anchor position of Ty 56-70 was hypothesized to be I58, L59, or L60 and the P6 anchor to be A63, P64 or L65 (FIG. 6). To confirm this, peptides with amino acid substitutions at these positions (Q=unfavorable substitution, F or V=favorable) and serially truncated peptides were tested for T cell recognition. The results shown in FIG. 6 suggest that I58 and A63 are the P1 and P6 anchors, respectively, of Ty 56-70 (FIG. 7). In addition, two modified peptides (Ty 56-70, A63→V and Ty 56-70, L65→V) seemed to evoke an enhanced T cell response compared to the unmodified Ty 56-70. This was confirmed by titrating the T cell response to these peptides (FIG. 8).

Figure 10:
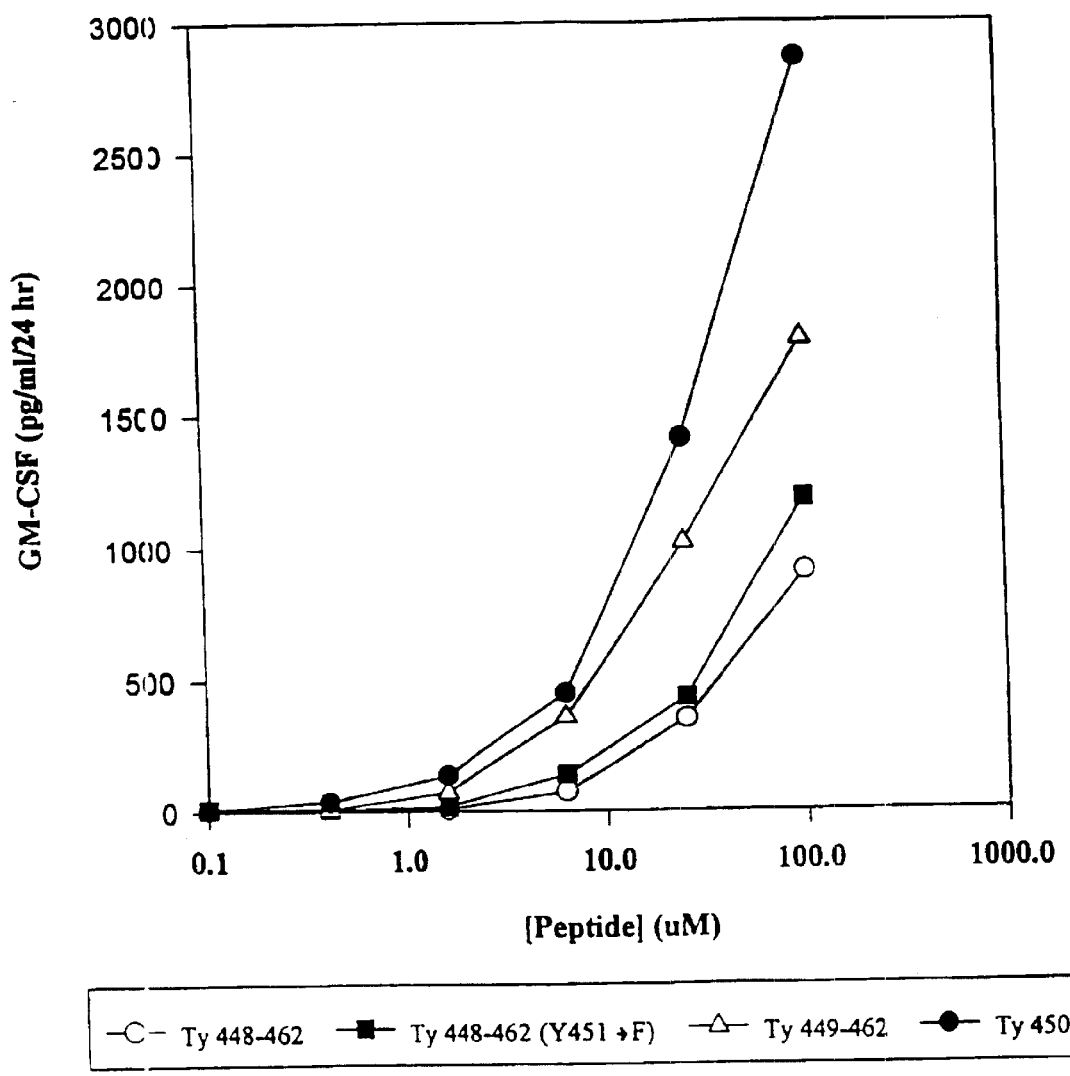
FIG. 10 shows CD4+ TIL 1088 recognize truncated tyrosinase 448-462 peptides, Ty 449-462 and Ty 450-462, better than Ty 448-462. (Background TIL+EBV=196 pg/ml, subtracted).

In repeated experiments, Ty 448-462 was specifically recognized by CD4+ T cells from patient 1088. By testing modified peptides with either unfavorable (Q) or favorable (F) amino acid substitutions at potential P1 anchor positions (FIG. 9), and by testing a series of truncated peptides, Y451 was identified as the P1 anchor. At this position, the unfavorable amino acid substitution abolished T cell recognition, while the favorable substitution restored it. In addition, it was found that the truncated Ty 449-462 and 450-462 peptides were more stimulatory for T cells than the parent peptide. This was confirmed in a subsequent titration experiment (see FIG. 10).

Figure 12:
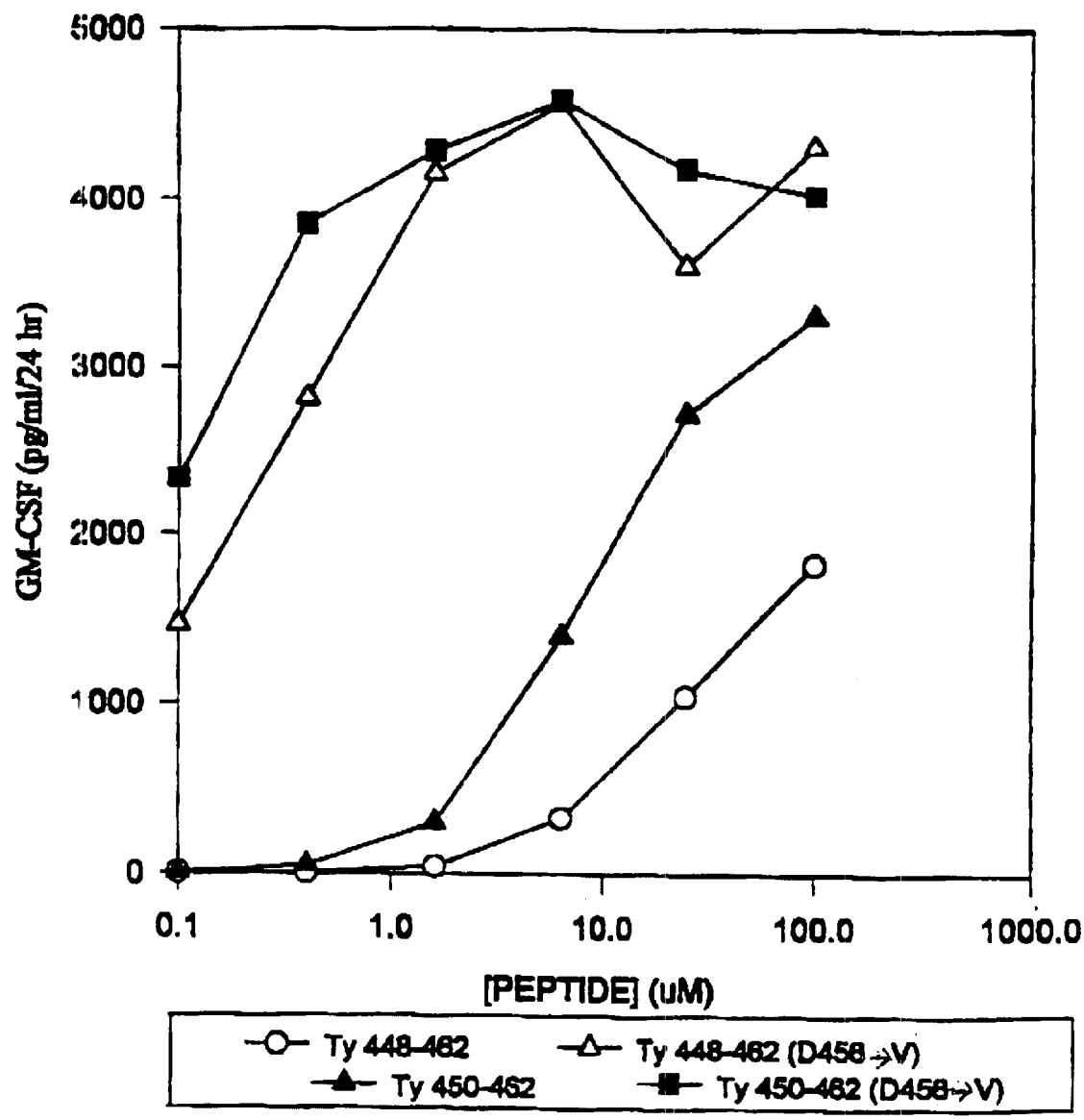
FIG. 12 shows CD4+ TIL 1088 recognize modified Tyrosinase 448-462 peptides better than the non-modified or nonmutated peptide (Background TIL+EBV=99 pg/ml, subtracted).

The P6 anchor position for Ty 448-462 was presumed to be D456, based on identifying Y451 as the P1 anchor. D (aspartic acid) is not an optimal residue at this position, and a valine substitution led to markedly enhanced T cell recognition (see FIG. 11). When two favorable modifications of Ty 448-462 were combined in a single modified peptide (Ty 450-462, D456→V), recognition was enhanced even more (see FIG. 12).

In summary, both Ty 56-70 and Ty 448-462 are restricted by HLA-DRB1*0401. This MHC molecule is expressed by approximately 15% of the North American Caucasian population. The anchor positions in Ty 56-70 and Ty 448-462 have been identified (see FIG. 7), and substitutions of amino acids at these positions have created modified peptides with enhanced T cell stimulatory properties.

The utility of these peptides in the prophylaxis and/or therapy of melanoma may not be limited to patients expressing the Class II MHC molecule DRB1*0401, as Class II-restricted peptides are often capable of binding to more than one Class II molecule (Chicz, R. M. et al (1993) *J. Exp. Med.* 178, 27–47; Malcherek, G. et al (1995) *J. Exp. Med.* 181, 527–536).

Although the present invention has been described in some detail by way of illustration, and examples for purposes of clarification and understanding it will be obvious that certain changes may be made within the scope of the appended claims. Indeed, various modifications of the invention in addition to those shown and described herein will become apparent to those skilled in the art from the foregoing description and accompanying drawings. Such modifications are intended to fall within the scope of the claims.

We claim:

1. An isolated immunogenic peptide consisting of a portion of SEQ ID NO: 39, wherein said portion comprises (i) at least 9 contiguous amino acids from amino acids 56–70 of SEQ ID NO: 39 or (ii) at least 9 contiguous amino acids from amino acids 448–462 of SEQ ID NO: 39, wherein the immunogenic peptide is 9 to 34 amino acids in length and is recognized by a $CD4^+$ T lymphocyte, which is restricted by a Major Histocompatibility Complex (MHC) Class II molecule.

2. The isolated immunogenic peptide of claim 1, wherein the peptide consists of amino acids 56–70 of SEQ ID NO: 39.

3. The isolated immunogenic peptide of claim 1, wherein the peptide consists of amino acids 448–462 of SEQ ID NO: 39.

4. The isolated immunogenic peptide of claim 1, wherein the peptide consists of amino acids 57–70 of SEQ ID NO: 39.

5. The isolated immunogenic peptide of claim 1, wherein the peptide consists of amino acids 449–462 of SEQ ID NO: 39.

6. The isolated immunogenic peptide of claim 1, wherein the peptide consists of amino acids 450–462 of SEQ ID NO: 39.

7. The immunogenic peptide of claim 1, wherein the MHC Class II molecule is Human Leukocyte Antigen (HLA)-DR.

8. The immunogenic peptide of claim 7, wherein the HLA-DR is HLA-DRB1*0401.

9. A single-chain Class II-MHC-peptide construct comprising the immunogenic peptide of claim 1 linked to an MHC Class II, molecule or an immunogenic peptide binding portion thereof.

10. The single-chain Class II-MHC-peptide construct of claim 9, wherein the immunogenic peptide binding portion of the MHC Class II molecule is the β chain of the MHC Class II molecule.

11. A composition comprising the immunogenic peptide of claim 1.

12. A composition comprising an MHC Class II molecule or an immunogenic peptide binding portion thereof linked to the immunogenic peptide of claim 1.

13. A method of inducing $CD4^+$ T lymphocytes to respond to melanoma, which method comprises:
   (i) contacting antigen presenting cells with a composition of claim 11 in vitro, and
   (ii) simultaneously or subsequently exposing $CD4^+$ T lymphocytes to the antigen presenting cells in vitro, whereupon the $CD4^+$ T lymphocytes are induced to respond to melanoma.

14. The method of claim 13, wherein the $CD4^+$ T lymphocytes are obtained from a host and the method further comprises:
   (iii) administering the $CD4^+$ T lymphocytes to the host.

15. The method of claim 14, wherein the host is a mammal.

16. The method of claim 15, wherein the mammal is a human.

17. The method of claim 14, wherein the antigen presenting cells are obtained from the host.

18. The method of inducing $CD4^+$ T lymphocytes in a host to respond to melanoma, which method comprises:
   (i) contacting antigen presenting cells with a composition of claim 11 in vitro, and
   (ii) subsequently exposing $CD4^+$ T lymphocytes in the host to the antigen presenting cells by administering the antigen presenting cells to the host, whereupon the CD4+ T lymphocytes in the host are induced to respond to melanoma.

19. The method of claim 18, wherein the host is a mammal.

20. The method of claim 19, wherein the mammal is a human.

21. The method of claim 18, wherein the antigen presenting cells are obtained from the host.

22. A method of inducing CD4+ T lymphocytes in a host to respond to melanoma, which method comprises administering the composition of claim 11 to the host, whereupon the CD4+ T lymphocytes in the host are induced to respond to melanoma.

23. A method of inducing CD4+ T lymphocytes to respond to melanoma, which method comprises:
   (i) contacting antigen presenting cells with a composition of claim 12 in vitro, and
   (ii) simultaneously or subsequently exposing CD4+ T lymphocytes to the antigen presenting cells in vitro,
whereupon the CD4+ T lymphocytes are induced to respond to melanoma.

24. The method of claim 23, wherein the CD4+ T lymphocytes are obtained from a host and the method further comprises:
   (iii) administering the CD4+ T lymphocytes to the host.

25. The method of claim 24, wherein the host is a mammal.

26. The method of claim 25, wherein the mammal is a human.

27. The method of claim 24, wherein the antigen presenting cells are obtained from the host.

28. A method of inducing CD4+ T lymphocytes in a host to respond to melanoma, which method comprises:
   (i) contacting antigen presenting cells with a composition of claim 12 in vitro, and
   (ii) subsequently exposing CD4+ T lymphocytes to the antigen presenting cells by administering the antigen presenting cells to the host,
whereupon the CD4+ T lymphocytes in the host are induced to respond to melanoma.

29. The method of claim 28, wherein the host is a mammal.

30. The method of claim 29, wherein the mammal is a human.

31. The method of claim 28, wherein the antigen presenting cells are obtained from the host.

32. A method of inducing CD4+ T lymphocytes in a host to respond to melanoma, which method comprises administering the composition of claim 12 to the host, whereupon the CD4+ T lymphocytes in the host are induced to respond to melanoma.

33. A derivative of an isolated immunogenic peptide consisting of a portion of SEQ ID NO: 39 comprising at least 9 contiguous amino acids from amino acids 56–70 of SEQ ID NO: 39, wherein the immunogenic peptide is 9 to 34 amino acids in length and is recognized by a CD4+ lymphocyte restricted by a Major Histocompatibility Complex (MHC) Class II molecule, wherein the derivative consists of a substitution of amino acid 65 of SEQ ID NO: 39 with a valine.

34. A derivative of an isolated immunogenic peptide consisting of a portion of SEQ ID NO: 39 comprising at least 9 contiguous amino acids from amino acids 448–462 of SEQ ID NO: 39, wherein the immunogenic peptide is 9 to 34 amino acids in length and is recognized by a CD4+ lymphocyte restricted by a Major Histocompatibility Complex (MHC) Class II molecule, wherein the derivative consists of a substitution of amino acid 451 of SEQ ID NO: 39 with a phenylalanine.

35. A derivative of an isolated immunogenic peptide consisting of a portion of SEQ ID NO: 39, wherein the portion comprises (a) at least 9 amino acids from amino acids 56–70 of SEQ ID NO: 39, wherein the derivative consists of an amino acid substitution selected from the group consisting of A63V, I58F, I58V, L60 F, and L60, or (b) at least 9 amino acids from amino acids 448–462 of SEQ ID NO: 39, wherein the derivative consists of an amino acid substitution selected from the group consisting of D456V, Y449F, and Y449Q, wherein the peptide is 9 to 34 amino acids in length, and wherein the derivative of an isolated immunogenic peptide is restricted by a MHC Class II molecule.

36. The derivative of an isolated immunogenic peptide of claim 35, wherein the MHC Class II molecule is HLA-DR.

37. The derivative of an isolated immunogenic peptide of claim 36, wherein the HLA-DR is HLA-DRB1*0401.

38. A single-chain Class II-MHC-peptide construct comprising the derivative of an isolated immunogenic peptide of claim 35 linked to an MHC Class II molecule or an immunogenic peptide binding portion thereof.

39. The single-chain Class II-MHC-peptide construct of claim 38, wherein the immunogenic peptide binding portion of the MHC Class II molecule is the β chain of the MHC Class II molecule.

40. A composition comprising the derivative of an isolated immunogenic peptide of claim 35.

41. A composition comprising an MHC Class II molecule or an immunogenic peptide binding portion thereof linked to the derivative of an isolated immunogenic peptide of claim 35.

42. A method of inducing CD4+ T lymphocytes to respond to melanoma, which method comprises:
   (i) contacting antigen presenting cells with a composition of claim 40 in vitro, and
   (ii) simultaneously or subsequently exposing CD4+ T lymphocytes to the antigen presenting cells in vitro,
whereupon the CD4+ T lymphocytes are induced to respond to melanoma.

43. The method of claim 42, wherein the CD4+ T lymphocytes are obtained from a host and the method further comprises:
   (iii) administering the CD4+ T lymphocytes to the host.

44. The method of claim 43, wherein the host is a mammal.

45. The method of claim 44, wherein the mammal is human.

46. The method of claim 43, wherein the antigen presenting cells are obtained from the host.

47. A method of inducing CD4+ T lymphocytes in a host to respond to melanoma, which method comprises:
   (i) contacting antigen presenting cells with a composition of claim 40 in vitro, and
   (ii) subsequently exposing CD4+ T lymphocytes in the host to the antigen presenting cells by administering the antigen presenting cells to the host,
whereupon the CD4+ T lymphocytes in the host are induced to respond to melanoma.

48. The method of claim 47, wherein the host is a mammal.

49. The method of claim 48, wherein the mammal is a human.

50. The method of claim 47, wherein the antigen presenting cells are obtained from the host.

51. A method of inducing CD4⁺ T lymphocytes in a host to respond to melanoma, which method comprises administered the composition of claim 40 to the host, whereupon the CD4⁺ T lymphocytes in the host are induced to respond to melanoma.

52. A method inducing CD4⁺ T lymphocytes to respond to melanoma, which method comprises:

(i) contacting antigen presenting cells with a composition of claim 41 in vitro, and (ii) simultaneously or subsequently exposing CD4⁺ T lymphocytes to the antigen presenting cells in vitro, whereupon the CD4⁺ T lymphocytes are induced to respond to melanoma.

53. The method of claim 52, wherein the CD4⁺ T lymphocytes are obtained from a host and the method further comprises:

(iii) administering the CD4⁺ T lymphocytes to the host.

54. The method of claim 53, wherein the host is a mammal.

55. The method of claim 54, wherein the mammal is a human.

56. The method of claim 53, wherein the antigen presenting cells are obtained from the host.

57. A method of inducing CD4⁺ T lymphocytes in a host to respond to melanoma, which method comprises:

(i) contacting antigen presenting cells with a composition of claim 41 in vitro, and (ii) subsequently exposing CD4⁺ T lymphocytes in the host to the antigen presenting cells by administering the antigen presenting cells to the host, whereupon the CD4⁺ T lymphocytes in the host are induced to respond to melanoma.

58. The method of claim 57, wherein the host is a mammal.

59. The method of claim 58, wherein the mammal is a human.

60. The method of claim 57, wherein the antigen presenting cells are obtained from the host.

61. A method of inducing CD4⁺ T lymphocytes in a host to respond to melanoma, which method comprises administering of claim 41 to the host, whereupon the CD4⁺ T lymphocytes in the host are induced to respond to melanoma.

* * * * *

UNITED STATES PATENT AND TRADEMARK OFFICE
CERTIFICATE OF CORRECTION

PATENT NO. : 6,951,917 B1
DATED : October 4, 2005
INVENTOR(S) : Topalian et al.

It is certified that error appears in the above-identified patent and that said Letters Patent is hereby corrected as shown below:

Title page,
Item [75], Inventors, "Suzane L. Topalian, Brookville, MD (US);" should read
-- Suzanne L. Topalian, Brookville, MD (US); --.

Signed and Sealed this

Twentieth Day of December, 2005

JON W. DUDAS
*Director of the United States Patent and Trademark Office*

SEQUENCE LISTING

```
<160> NUMBER OF SEQ ID NOS: 39

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Gln Asn Ile Leu Leu Ser Asn Ala Pro Leu Gly Pro Gln Phe Pro
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Asn Ile Leu Leu Ser Asn Ala Pro Leu Gly Pro Gln Phe Pro
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Gln Asn Ile Leu Leu Ser Asn Ala Pro Val Gly Pro Gln Phe Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Gln Asn Ile Leu Leu Ser Asn Val Pro Val Gly Pro Gln Phe Pro
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic
```

<400> SEQUENCE: 5

Gln Asn Ile Leu Leu Ser Asn Val Pro Leu Gly Pro Gln Phe Pro
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Asp Tyr Ser Tyr Leu Gln Asp Ser Asp Pro Asp Ser Phe Gln Asp
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Asp Tyr Ser Tyr Leu Gln Asp Ser Asp Pro Asp Ser Ser Gln Asp
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Asp Gln Ser Tyr Leu Gln Asp Ser Asp Pro Asp Ser Phe Gln Asp
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Asp Phe Ser Tyr Leu Gln Asp Ser Asp Pro Asp Ser Phe Gln Asp
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Asp Tyr Ser Phe Leu Gln Asp Ser Asp Pro Asp Ser Phe Gln Asp
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic

```
<400> SEQUENCE: 11

Asp Tyr Ser Tyr Leu Gln Asp Ser Val Pro Asp Ser Phe Gln Asp
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ser Tyr Leu Gln Asp Ser Val Pro Asp Ser Phe Gln Asp
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Tyr Ser Tyr Leu Gln Asp Ser Asp Pro Asp Ser Phe Gln Asp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic

<400> SEQUENCE: 14

Ser Tyr Leu Gln Asp Ser Asp Pro Asp Ser Phe Gln Asp
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Leu, Ile, Met, Val, Trp, Phe or Tyr
<220> FEATURE:
<221> NAME/KEY: misc_feature
<222> LOCATION: (4)..(4)
<223> OTHER INFORMATION: Xaa = Asp, Glu, or Xaa
<220> FEATURE:
<221> NAME/KEY: misc_feature
<222> LOCATION: (6)..(6)
<223> OTHER INFORMATION: Xaa = Xaa, Ser, or Thr
<220> FEATURE:
<221> NAME/KEY: misc_feature
<222> LOCATION: (7)..(7)
<223> OTHER INFORMATION: Xaa = Asp, Ala, Ser, Val, His, Pro, Asn, Met,
      Thr, Leu, or Ile
<220> FEATURE:
<221> NAME/KEY: misc_feature
<222> LOCATION: (9)..(9)
<223> OTHER INFORMATION: Xaa = Ala, Ser, Gln, Gly, Leu, Val, or Thr

<400> SEQUENCE: 15

Xaa Leu Leu Xaa Asn Xaa Xaa Leu Xaa
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa = Leu, Ile, Met, Val, Trp, Phe, or Tyr
<220> FEATURE:
<221> NAME/KEY: misc_feature
<222> LOCATION: (1)..(1)
<223> OTHER INFORMATION: Xaa = Leu, Ile, Met, Val, Trp, Phe, or Tyr
<220> FEATURE:
<221> NAME/KEY: misc_feature
<222> LOCATION: (4)..(4)
<223> OTHER INFORMATION: Xaa = Asp, Glu, or Xaa
<220> FEATURE:
<221> NAME/KEY: misc_feature
<222> LOCATION: (6)..(6)
<223> OTHER INFORMATION: Xaa = Xaa, Ser, or Thr
<220> FEATURE:
<221> NAME/KEY: misc_feature
<222> LOCATION: (7)..(7)
<223> OTHER INFORMATION: Xaa = Asp, Ala, Ser, Val, His, Pro, Asn, Met,
      Thr, Leu, or Ile
<220> FEATURE:
<221> NAME/KEY: misc_feature
<222> LOCATION: (9)..(9)
<223> OTHER INFORMATION: Xaa = Ala, Ser, Gln, Gly, Leu, Val, or Thr

<400> SEQUENCE: 16

Xaa Leu Gln Xaa Ser Xaa Xaa Asp Xaa
1               5

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Gln Asn Gln Leu Leu Ser Asn Ala Pro Leu Gly Pro Gln Phe Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Gln Asn Phe Leu Leu Ser Asn Ala Pro Leu Gly Pro Gln Phe Pro
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Gln Asn Val Leu Leu Ser Asn Ala Pro Leu Gly Pro Gln Phe Pro
1               5                   10                  15

<210> SEQ ID NO 20
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 20

Gln Asn Ile Gln Leu Ser Asn Ala Pro Leu Gly Pro Gln Phe Pro
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Gln Asn Ile Phe Leu Ser Asn Ala Pro Leu Gly Pro Gln Phe Pro
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic

<400> SEQUENCE: 22

Gln Asn Ile Val Leu Ser Asn Ala Pro Leu Gly Pro Gln Phe Pro
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Gln Asn Ile Leu Gln Ser Asn Ala Pro Leu Gly Pro Gln Phe Pro
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Gln Asn Ile Leu Phe Ser Asn Ala Pro Leu Gly Pro Gln Phe Pro
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Gln Asn Ile Leu Val Ser Asn Ala Pro Leu Gly Pro Gln Phe Pro
1               5                   10                  15

<210> SEQ ID NO 26
<211> LENGTH: 15
<212> TYPE: PRT
```

```
<213> ORGANISM: Artificial Sequence
<220> FEATURE:
<223> OTHER INFORMATION: Synthetic

<400> SEQUENCE: 26

Gln Asn Ile Leu Leu Ser Asn Gln Pro Leu Gly Pro Gln Phe Pro
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Gln Asn Ile Leu Leu Ser Asn Ala Gln Leu Gly Pro Gln Phe Pro
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Gln Asn Ile Leu Leu Ser Asn Ala Val Leu Gly Pro Gln Phe Pro
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Gln Asn Ile Leu Leu Ser Asn Ala Pro Gln Gly Pro Gln Phe Pro
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: Synthetic

<400> SEQUENCE: 30

Ile Leu Leu Ser Asn Ala Pro Leu Gly Pro Gln Phe Pro
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic

<400> SEQUENCE: 31

Leu Leu Ser Asn Ala Pro Leu Gly Pro Gln Phe Pro Phe
1               5                   10

<210> SEQ ID NO 32
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 32

Leu Ser Asn Ala Pro Leu Gly Pro Gln Phe Pro Phe Thr
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic

<400> SEQUENCE: 33

Ser Asn Ala Pro Leu Gly Pro Gln Phe Pro Phe Thr Gly Val Asp
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Asp Tyr Ser Gln Leu Gln Asp Ser Asp Pro Asp Ser Phe Gln Asp
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Asp Tyr Ser Tyr Gln Gln Asp Ser Asp Pro Asp Ser Phe Gln Asp
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Asp Tyr Ser Tyr Phe Gln Asp Ser Asp Pro Asp Ser Phe Gln Asp
1               5                   10                  15

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Tyr Leu Gln Asp Ser Asp Pro Asp Ser Phe Gln Asp
1               5                   10

<210> SEQ ID NO 38
<211> LENGTH: 11
<212> TYPE: PRT
<213> ORGANISM: Artificial Sequence
<220> FEATURE:
```

-continued

<223> OTHER INFORMATION: Synthetic

<400> SEQUENCE: 38

Leu Gln Asp Ser Asp Pro Asp Ser Phe Gln Asp
1               5                   10

<210> SEQ ID NO 39
<211> LENGTH: 529
<212> TYPE: PRT
<213> ORGANISM: Homo sapiens

<400> SEQUENCE: 39

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
        50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
                100                 105                 110

Thr Glu Arg Arg Leu Leu Val Arg Arg Asn Ile Phe Asp Leu Ser Ala
            115                 120                 125

Pro Glu Lys Asp Lys Phe Phe Ala Tyr Leu Thr Leu Ala Lys His Thr
        130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
                180                 185                 190

Glu Ile Trp Arg Asp Ile Asp Phe Ala His Glu Ala Pro Ala Phe Leu
            195                 200                 205

Pro Trp His Arg Leu Phe Leu Leu Arg Trp Glu Gln Glu Ile Gln Lys
        210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
                260                 265                 270

Gln Ile Val Cys Ser Arg Leu Glu Glu Tyr Asn Ser His Gln Ser Leu
            275                 280                 285

Cys Asn Gly Thr Pro Glu Gly Pro Leu Arg Arg Asn Pro Gly Asn His
        290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr

-continued

```
                    340                 345                 350
Gly Ile Ala Asp Ala Ser Gln Ser Ser Met His Asn Ala Leu His Ile
        355                 360                 365

Tyr Met Asn Gly Thr Met Ser Gln Val Gln Gly Ser Ala Asn Asp Pro
        370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
                420                 425                 430

Tyr Arg Asn Gly Asp Phe Phe Ile Ser Ser Lys Asp Leu Gly Tyr Asp
        435                 440                 445

Tyr Ser Tyr Leu Gln Asp Ser Asp Pro Asp Ser Phe Gln Asp Tyr Ile
        450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
                500                 505                 510

Pro Leu Leu Met Glu Lys Glu Asp Tyr His Ser Leu Tyr Gln Ser His
        515                 520                 525

Leu
```